(12) United States Patent
Schudok et al.

(10) Patent No.: US 7,772,270 B2
(45) Date of Patent: Aug. 10, 2010

(54) IMINO ACID DERIVATIVES AS INHIBITORS OF MATRIX METALLOPROTEINASES

(75) Inventors: Manfred Schudok, Eppstein (DE); Sven Ruf, Mainz (DE); Hans Matter, Langenselbold (DE); Volkmar Wehner, Sandberg (DE); Reinhard Kirsch, Braunschweig (DE); Petra Lennig, Mainz (DE)

(73) Assignee: sanofi-aventis Deutschland GmbH, Frankfurt am Main (DE)

( * ) Notice: Subject to any disclaimer, the term of this patent is extended or adjusted under 35 U.S.C. 154(b) by 304 days.

(21) Appl. No.: 11/405,834

(22) Filed: Apr. 18, 2006

(65) Prior Publication Data

US 2006/0252752 A1 Nov. 9, 2006

Related U.S. Application Data

(63) Continuation-in-part of application No. 10/751,600, filed on Jan. 5, 2004, now abandoned.

(60) Provisional application No. 60/472,572, filed on May 22, 2003.

(30) Foreign Application Priority Data

Jan. 3, 2003 (DE) ................................ 103 00 015

(51) Int. Cl.
*A61K 31/403* (2006.01)
*C07D 209/52* (2006.01)
(52) U.S. Cl. ........................ 514/412; 514/414; 548/452; 548/465
(58) Field of Classification Search .................. 548/452, 548/465
See application file for complete search history.

(56) References Cited

U.S. PATENT DOCUMENTS

| 5,795,890 | A | 8/1998 | Nakae |
| 6,207,672 | B1 | 3/2001 | Thorwart |
| 6,573,277 | B2 | 6/2003 | Thorwart |
| 6,855,708 | B2 | 2/2005 | Lin et al. |

FOREIGN PATENT DOCUMENTS

| EP | 0769498 | 4/1997 |
| EP | 0606046 | 10/1997 |
| WO | WO 94/26889 | 12/1994 |
| WO | WO 96/27583 | 9/1996 |
| WO | WO0058304 | 10/2000 |
| WO | WO 01/62733 | 8/2001 |

OTHER PUBLICATIONS

RN 810685-46-2, retrieved from CAPLUS on May 21, 2008.*
Cancer and Metastasis Reviews (1998), 17(1), 91-106.*
Science (1999), vol. 286, 531-537.*
Cancer [online], [retrieved on Jul. 6, 2007]. Retrieved from the internet, URL http://www.nlm.nih.gov/medlineplus/cancer.html>.*
Cancer [online], [retrieved on Jul. 6, 2007], retrieved from the internet, URL; http://en.wikipedia.org/wiki/Cancer.*
Osteoarthritis [online], [retrieved on Aug. 26, 2009], retrieved from the internet, URL; http://www.emedicinehealth.com/script/main/art.asp?articlekey=59253&pf=3&page1.*
Arthritis [online], [retrieved on Aug. 26, 2009], retrieved from the internet, URL; http://www.healthline.com/adamcontent/arthritis.*
Reactive perforating collagenosis [online], [retrieved on Aug. 26, 2009], retrieved from the internet, URL; http://emedicine.medscape.com/article/1074803.*
Stroke [online], [retrieved on Aug. 26, 2009], retrieved from the internet, URL; http://www.healthline.com/adamcontent/stroke.*
Cervical spondylosis [online], [retrieved on Aug. 26, 2009], retrieved from the internet, URL; http://www.nlm.nih.gov/medlineplus/ency/article/000436.htm.*
Cohn, et al., The Management of Chronic Heart Failure, N. Engl. J. Med.; 335(7); Aug. 1996, pp. 490-498; Table 2.
Haskins, et al., Sulfonamides as Novel Terminators of Cationic Cyclisations. Chem Commun. (Royal Chemical Society); 22; 2002; pp. 2724-2725.
Hodgson, et al., Development Of Dirhodium(II)-Catalyzed Generation and Enantioselective 1,3-Dipolar Cycloaddition Of Carbonyl Ylides, Chem. Eur. J, (2001). 7, No. 20, 4465-4476.
Massova, et al., Matrix Metalloproteinases: Structures, Evolution, and Diversification, The FASEB Journal (1998) 12, 1075-1095.
Michaelides, et al., Recent Advances In Matrix Metalloproteinase Inhibitors Research, Current Pharmaceutical Design 5 (1999) 787-819.
Nuhrich, et al., Cyclization of N-tosyloxlranylpropylamines, Synthesis of Nitrogen Heterocycles, HCAPLUS Database; STN International; 2006; Accession No. 115:49298.

(Continued)

*Primary Examiner*—Rebecca L Anderson
*Assistant Examiner*—Shawquia Young
(74) *Attorney, Agent, or Firm*—James W. Bolcsak

(57) ABSTRACT

The invention relates to a bicycloazaheterocyclyl carboxylic acid sulfonamide derivative of formula I herein, pharmaceutical preparation comprising it, process for preparing it and method for its pharmaceutical use.

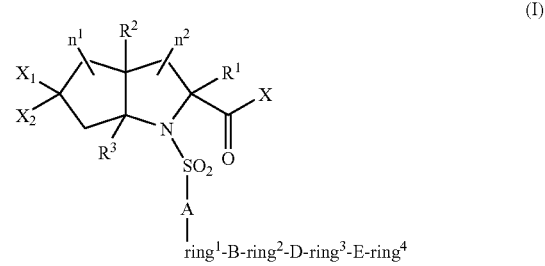

(I)

5 Claims, No Drawings

OTHER PUBLICATIONS

Witulski, et al., Stereospecific Synthesis of Chiral N-(ethynl)allylglycines and their use in Highly Stereoselective Intramolecular Pauson-Khand Reactions, Chem. Commun. 18; 1999; pp. 1879-1860.

Ye, et al., Purification And Characterization Of The Human Stromelysin Catalytic Domain Expressed In *Escherichia coli*, Biochemistry 31 (1992), 11231-11235.

Yip, et al., Matrix Metalloproteinase Inhibitors: Applications In Oncology, Investigational New Drugs 17 (1999), 367-399.

* cited by examiner

IMINO ACID DERIVATIVES AS INHIBITORS OF MATRIX METALLOPROTEINASES

CROSS REFERENCE TO RELATED APPLICATIONS

This application is a continuation-in-part of U.S. application Ser. No. 10/751,600, filed Jan. 5, 2004, which claims priority under 35 U.S.C. §119(e) to U.S. provisional application No. 60/472,572, filed May 22, 2003 and under 35 U.S.C. §119(a) to German Application No. 10300015.1, filed Jan. 3, 2003.

FIELD OF THE INVENTION

The invention relates to a bicycloazaheterocyclyl carboxylic acid sulfonamide derivative of formula I herein, pharmaceutical preparation comprising it, process for preparing it and method for its pharmaceutical use.

BACKGROUND OF THE INVENTION

In diseases such as osteoarthritis and rheumatism, the joint is destroyed, with this destruction being due, in particular, to the proteolytic breakdown of collagen by collagenases. Collagenases belong to the superfamily of the metalloproteinases (MPs) or matrix metalloproteinases (MMPs). The MMPs form a group of Zn-dependent enzymes which are involved in the biological breakdown of the extracellular matrix (D. Yip et al. in Investigational New Drugs 17 (1999), 387-399 and Michaelides et al. in Current Pharmaceutical Design 5 (1999) 787-819). These MMPs are able, in particular, to break down fibrillar and nonfibrillar collagen and proteoglycans, both of which are important matrix constituents. MMPs are involved in processes of wound healing, tumor invasion, metastasis migration and in angiogenesis, multiple sclerosis and heart failure (Michaelides page 788; see above). In particular, they play an important role in the breakdown of the joint matrix in arthrosis and arthritis, whether it is osteoarthrosis, osteoarthritis or rheumatoid arthritis.

The activity of the MMPs is furthermore essential for many of the processes which play a role in the formation of atherosclerotic plaques, such as the infiltration of inflammatory cells, the migration of smooth muscle cells, and proliferation and angiogenesis (S. J. George, Exp. Opin. Invest. Drugs (2000), 9 (5), 993-1007). In addition, degradation of the matrix by MMPs can cause anything from plaque instabilities through to ruptures, with this being able to lead to the clinical symptoms of atherosclerosis, unstable angina pectoris, myocardial infarction or stroke (E. J. M. Creemers et al., Circulation Res. 89, 201-210 (2001)). All in all, the complete MMP family is able to break down all the components of the blood vessel extracellular matrix; for this reason, their activity is to a high degree subject to regulatory mechanisms in normal blood vessels. The increase in MMP activity during plaque formation and plaque instability is caused by an increase in cytokine-stimulated and growth factor-stimulated gene transcription, an increase in zymogen activation and an imbalance in the MMP/TIMP (tissue inhibitors of metalloproteases) ratio. It therefore seems plausible that MMP inhibition or the reattainment of the MMP/TIMP equilibrium would be of assistance in treating the atherosclerotic diseases. It is also becoming ever clearer that aside from atherosclerosis, an increase in MMP activity is also at least a contributory cause of other cardiovascular diseases such as restenosis, dilated cardiomyopathy and the already mentioned myocardial infarction. It has been shown that administering synthetic inhibitors in experimental animal models can achieve marked improvements in these diseases as regards, for example, formation of atherosclerotic lesions, neointima formation, left-ventricular remodeling, pumping output malfunction or infarction healing. In a variety of preclinical studies using MMP inhibitors, detailed tissue analysis indicated a reduction in collagen damage, an improvement in extracellular matrix remodeling and an improvement in the structure and function of cardiac muscle and blood vessels. Of these processes, matrix remodeling processes and MMP-regulated fibroses are regarded, in particular, as being important components in the progress of cardiac diseases (infarction) (Drugs 61, 1239-1252 (2001)).

MMPs cleave matrix proteins, such as collagen, laminin, proteoglycans, elastin or gelatin, and also process (i.e., activate or deactivate), by means of a cleavage, a large number of other proteins and enzymes under physiological conditions, which means that they play an important role in the entire organism, with this role being of particular importance in connective tissue and bone.

A large number of different inhibitors of the MMPs are known (EP0606046; WO94/28889; WO 96/27583; or also overviews such as Current Medicinal Chemistry 8, 425-74 (2001)). Following the first clinical studies in humans, it has now been found that MMPs give rise to side effects. The side effects that are principally mentioned are musculoskeletal pains or anthralgias. The prior art states unambiguously that it is expected that more selective inhibitors will be able to reduce these said side effects (Yip, page 387, see above). Particular emphasis should be placed in this case on specificity in respect to MMP-1, as these undesirable side effects obviously occur to a greater extent with inhibition of MMP-1.

The known MMP inhibitors therefore frequently suffer from the disadvantage of lacking specificity. Most MMP inhibitors inhibit many MMPs simultaneously because the structure of the catalytic domain in the MMPs is similar. As a consequence, the inhibitors have the undesirable property of acting on the enzymes including those that have a vital function (Massova, I., et al., The FASEB Journal (1998) 12, 1075-1095).

In view of the current situation, it is clear that there is a need for a compound that is a powerful inhibitor of the matrix metalloproteinases MMP-2, MMP-3, MMP-8, MMP-9 and MMP-13 whereas it has only a weak inhibitory effect on MMP-1.

SUMMARY OF THE INVENTION

The present invention satisfies the above needs by providing a compound that is a powerful inhibitor of the matrix metalloproteinases MMP-2, MMP-3, MMP-8, MMP-9 and MMP-13 whereas it has only a weak inhibitory effect on MMP-1.

The invention therefore relates to a compound of formula I

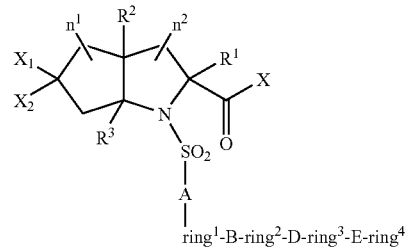

wherein

A is
- —($C_0$-$C_4$)-alkylene,

B, D and E are identical or different and are, independently of each other,
- —($C_0$-$C_4$)-alkylene,
- —($C_2$-$C_4$)-alkenylene,
- —S(O)$_o$—,
- —NH—,
- —NH—C(O)—,
- —C(O)—NH—,
- —NH—SO$_2$—,
- —NH—C(O)—NH—,
- —NH—C(S)—,
- —NH—C(O)—O—,
- —O—,
- —O—C(O)—NH—,
- —C(O)—,
- —O—(CH$_2$)$_n$—O—, or
- —O—(CH$_2$)$_m$—NH—, o is
- zero, 1 or 2, n is
- 2 or 3, m is
- 2 or 3, ring$^1$, ring$^2$ or ring$^3$ are identical or different and are, independently of each other, covalent bond,
- —($C_6$-$C_{14}$)-aryl that is unsubstituted or substituted, independently of each other, once, twice or three times, by G, or
- 5- or 6-membered aromatic heteroaryl ring that is unsubstituted or substituted, independently of each other, once, twice or three times, by G, ring$^4$ is
- —($C_6$-$C_{14}$)-aryl that is unsubstituted or substituted, independently of each other, once, twice or three times, by G,
- 5- or 6-membered aromatic heteroaryl ring that is unsubstituted or substituted, independently of each other, once, twice or three times, by G,
- heteroaryl that is unsubstituted or substituted, independently of each other, once, twice or three times, by G, or
- azaheterocyclyl selected from the group consisting of

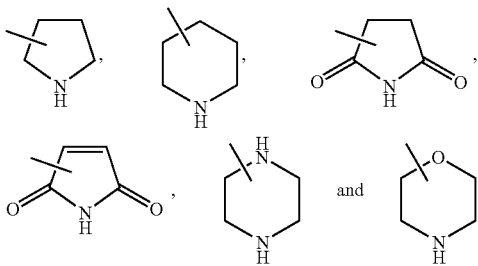

that is unsubstituted or substituted, independently of each other, once, twice or three times, by G, G is
- hydrogen,
- halogen,
- R$^4$
- —O—R$^4$,
- —C(O)—R$^5$,
- —S(O)$_p$—R$^4$,
- —NO$_2$,
- —CN or
- —NR$^3$R$^4$, p is
- zero, 1 or 2, X is
- —OH or —NH—OH, $X_1$ and $X_2$ are identical or different and are, independently of each other, hydrogen or —($C_1$-$C_6$)-alkyl, or taken together form the radical =O, n$^1$ is
- —(CH$_2$)$_r$—, n$^2$ is
- —(CH$_2$)$_q$—, r is
- zero, 1, 2 or 3, q is
- zero, 1, 2 or 3, R$^1$ is
- hydrogen, or
- —($C_1$-$C_6$)-alkyl that is unsubstituted or substituted, once or twice, by —($C_3$-$C_6$)-cycloalkyl, —($C_6$-$C_{14}$)-aryl or heteroaryl, R$^2$ and R$^3$ are identical or different and are, independently of each other,
- hydrogen or —($C_1$-$C_6$)-alkyl, R$^4$ is
- hydrogen,
- —($C_1$-$C_6$)-alkyl that is unsubstituted or substituted, once, twice or three times, by halogen, —($C_3$-$C_6$)-cycloalkyl, —($C_6$-$C_{14}$)-aryl or heteroaryl,
- —($C_6$-$C_{14}$)-aryl,
- heteroaryl,
- —C(O)—O—R$^5$,
- —C(S)-O—R$^5$,
- —C(O)—NH—R$^6$,
- —C(S)—NH—R$^6$, R$^5$ is —($C_1$-$C_6$)-alkyl that is unsubstituted or substituted, once or twice, by —($C_3$-$C_6$)-cycloalkyl, —($C_6$-$C_{14}$)-aryl, or heteroaryl,
- —($C_6$-$C_{14}$)-aryl, or
- heteroaryl, and R$^6$ is
- —($C_1$-$C_6$)-alkyl that is unsubstituted or substituted, once or twice, by —($C_3$-$C_6$)-cycloalkyl, —($C_6$-$C_{14}$)-aryl or heteroaryl, or
- —($C_6$-$C_{14}$)-aryl, or
- heteroaryl, or a stereoisomer thereof, a mixture of stereoisomers thereof in any ratio, or a physiologically tolerable salt thereof, provided that the compound is other than N-[(3,5-dichlorobenzene) sulfonyl]-(3a(S), 7a(S))-octahydro-indole-2(S)-carboxylic acid and its stereoisomers and N-tosylperhydrocyclopenta[b]pyrrole-2-carboxylic acid and its stereoisomers.

The invention also is directed to a method for preparing the compound according to the invention, a pharmaceutical preparation thereof, and its use for inhibiting matrix metalloproteinases MMP-2, MMP-3, MMP-8, MMP-9 and MMP-13.

DETAILED DESCRIPTION OF THE INVENTION

Definitions

As used above, and throughout the description of the invention, the following terms, unless otherwise indicated, shall be understood to have the following meanings:

The term "$(C_1-C_6)$-alkyl" means hydrocarbon radicals whose carbon chain is straight or branched and contains from 1 to 6 carbon atoms, for example methyl, ethyl, propyl, isopropyl, butyl, isobutyl, tertiary butyl, pentyl, isopentyl, neopentyl, hexyl, 2,3-dimethylbutane or neohexyl.

The term "—$(C_0-C_4)$-alkylene" means hydrocarbon radicals whose carbon chain is straight or branched and contains from 1 to 4 carbon atoms, for example methylene, ethylene, propylene, isopropylene, isobutylene, butylene or tertiary butylene. "—$C_0$-alkylene" is a covalent bond.

The term "—$(CH_2)_n$—, in which n is zero, 1 or 2" means, for n equal to zero, a covalent bond, for n equal to 1, the methylene radical and for n equal to 2, the ethylene radical.

The term "—$(C_2-C_4)$-alkenylene" means hydrocarbon radicals whose carbon chain is straight or branched and contains from 2 to 4 carbon atoms and, depending on the chain length, possesses one or two double bonds, for example ethenylene, propenylene, isopropenylene, isobutenylene or butenylene; provided the possibility exists in principle, the substituents on the double bond can be arranged in the E configuration or the Z configuration.

The term "—$(C_2-C_6)$-alkynylene" means hydrocarbon radicals whose carbon chain is straight or branched and contains from 2 to 6 carbon atoms and, depending on the chain length, possess 1 or 2 triple bonds, for example ethynylene, propenylene, isopropynylene, isobuthylynylene, butynylene, pentynylene or isomers of pentynylene or hexynylene or isomers of hexynylene.

The term "$(C_3-C_6)$-cycloalkyl" means a radical that is derived from 3- to 6-membered monocycles such as cyclopropyl, cyclobutyl, cyclopentyl or cyclohexyl.

The radicals

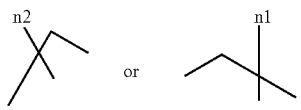

in the ring of the compound of formula I mean respectively —$(CH_2)_r$— and —$(CH_2)_q$— radicals wherein r and q are independently zero, 1, 2 or 3, where the variables $n^1$ or $n^2$ in each case indicate the number of the —$CH_2$— radicals in the ring of the formula I. When $n^1$ or $n^2$ has the value zero, a covalent bond is formed resulting in the ring consisting of a total of 4 ring atoms. When $n^1$ or $n^2$ has the value 1, a —$CH_2$— radical is formed resulting in the ring consisting of 5 ring atoms. When $n^1$ or $n^2$ has the value 2, a —$CH_2$—$CH_2$— radical is formed resulting in the ring consisting of 6 ring atoms. When $n^1$ or $n^2$ has the value 3, a —$CH_2$—$CH_2$—$CH_2$— radical is formed resulting in the ring consisting of 7 ring atoms.

The term "—$(C_6-C_{14})$-aryl" means aromatic carbon radicals having from 6 to 14 carbon atoms in the ring. —$(C_6-C_{14})$-aryl radicals are, for example, phenyl, naphthyl, for example 1-naphthyl or 2-naphthyl, anthryl or fluorenyl. Naphthyl radicals and, in particular, phenyl radicals are preferred aryl radicals.

The term "5- or 6-membered aromatic heteroaryl ring" means aromatic ring systems that contain one or two heteroatoms from the series oxygen, nitrogen and sulfur and can be derived from dihydrofuran, dioxole, dioxane, furan, imidazolidine, imidazoline, imidazole, isoxazole, isoxazolidine, 2-isoxazoline, isothiazole, isothiazolidine, 2-isothiazoline, morpholine, oxazole, oxothiolane, piperazine, piperidine, pyran, pyrazine, pyrazole, pyrazolidine, pyrazoline, pyridazine, pyridine, pyrimidine, pyrrole, pyrrolidine, tetrahydrofuran, tetrahydropyridine, thiazole, thiomorpholine, thiophenyl or thiopyran.

The term "heteroaryl" means a radical such as acridinyl, azepinyl, azetidinyl, aziridinyl, benzimidazalinyl, benzimidazolyl, benzofuranyl, benzothiofuranyl, benzothiophenyl, benzoxazolyl, benzothiazolyl, benzotriazolyl, benzotetrazolyl, benzisoxazolyl, benzisothiazolyl, carbazolyl, 4aH-carbazolyl, carbolinyl, chromanyl, chromenyl, cinnolinyl, decahydroquinolinyl, dibenzofuranyl, dibenzothiophenyl, dihydrofuran[2,3-b]tetrahydrofuranyl, dihydrofuranyl, dioxolyl, dioxanyl, 2H,6H-1,5,2-dithiazinyl, furanyl, furazanyl, imidazolidinyl, imidazolinyl, imidazolyl, 1H-indazolyl, indolinyl, indolizinyl, indolyl, 3H-indolyl, isobenzofuranyl, isochromanyl, isoindazolyl, isoindolinyl, isoindolyl, isoquinolinyl(benzimidazolyl), isothiazolidinyl, 2-isothiazolinyl, isothiazolyl, isoxazolyl, isoxazolidinyl, 2-isoxazolinyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxothiolanyl, pyrimidinyl, phenanthridinyl, phenanthrolinyl, phenazinyl, phenothiazinyl, phenoxathiinyl, phenoxazinyl, phthalazinyl, piperazinyl, piperidinyl, pteridinyl, purinyl, pyranyl, pyrazinyl, pyroazolidinyl, pyrazolinyl, pyrazolyl, pyridazinyl, pyridooxazolyl, pyridoimidazolyl, pyridothiazolyl, pyridothiophenyl, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, tetrahydropyridinyl, 6H-1,2,5-thiadazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiomorpholinyl, thiophenyl, triazinyl, 1,2,3-triazolyl, 1,2,3-triazolyl, 1,2,4-triazolyl, 1,2,5-triazolyl, 1,3,4-triazolyl and xanthenyl.

The term "azaheterocyclyl" means a 5 or 6 membered carbocyclic ring wherein one ring carbon thereof is replaced by a nitrogen atom and has other ring carbon atoms thereof optionally replaced by a heteroatom such as a nitrogen or oxygen. The azaheterocyclyl is also partially unsaturated or substituted by one or two oxo. Particular azaheterocyclyl are selected from the group consisting of

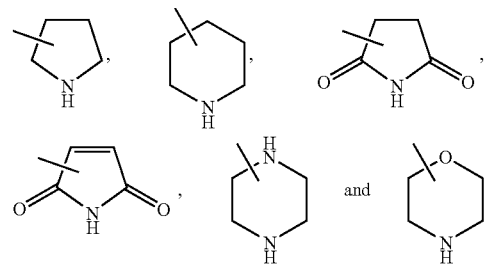

The term "bicycloazaheterocyclyl carboxylic acid sulfonamide derivative" pertains to the compound of formula I as defined.

Embodiments

Another embodiment of the invention relates to the compound of formula I as defined above wherein $ring^1$, $ring^2$ or $ring^3$ are —$(C_6-C_{14})$-aryl is phenyl, naphthyl, 1-naphthyl, 2-naphthyl, biphenylyl, 2-biphenylyl, 3-biphenylyl, 4-biphenylyl, anthryl or fluorenyl and is unsubstituted or substituted, independently of each other, once, twice or three times, by G, or 5- or 6-membered aromatic heteroaryl ring is dihydrofuranyl, dioxolyl, dioxanyl, furanyl, imidazolidinyl, imidazolinyl, imidazolyl, isoxazolyl, isoxazolidinyl, 2-isoxazolinyl, isothiazolyl, isothiazolidinyl, 2-isothiazolinyl, morpholinyl, oxazolyl, oxothiolanyl, piperazinyl, piperidinyl, pyranyl, pyrazinyl, pyrazolyl, pyrazolidinyl, pyrazolinyl, pyridazinyl, pyridinyl, pyrimidinyl, pyrrolyl, pyrrolidinyl, tetrahydrofuranyl, tetrahydropyridinyl, thiazolyl, thiomorpholinyl, thiophenyl or thiopyranyl and is unsubstituted or substituted, independently of each other, once, twice or three times, by G, ring$^4$ is
—$(C_6-C_{14})$-aryl that is phenyl, naphthyl, 1-naphthyl, 2-naphthyl, biphenylyl, 2-biphenylyl, 3-biphenylyl, 4-biphenylyl, anthryl or fluorenyl and is unsubstituted or substituted, independently of each other, once, twice or three times, by G, 5- or 6-membered aromatic heteroaryl ring that is dihydrofuranyl, dioxolyl, dioxanyl, furanyl, imidazolidinyl, imidazolinyl, imidazolyl, isoxazolyl, isoxazolidinyl, 2-isoxazolinyl, isothiazolyl, isothiazolidinyl, 2-isothiazolinyl, morpholinyl, oxazolyl, oxothiolanyl, piperazinyl, piperidinyl, pyranyl, pyrazinyl, pyrazolyl, pyrazolidinyl, pyrazolinyl, pyridazinyl, pyridinyl, pyrimidinyl, pyrrolyl, pyrrolidinyl, tetrahydrofuranyl, tetrahydropyridinyl, thiazolyl, thiomorpholinyl, thiophenyl or thiopyranyl and is unsubstituted or substituted, independently of each other, once, twice or three times, by G, or heteroaryl that is acridinyl, azetidinyl, benzimidazolyl, benzofuranyl, benzothiofuranyl, benzothiophenyl, benzoxazolyl, benzothiazolyl, benzotriazolyl, benzotetrazolyl, benzisoxazolyl, benzisothiazolyl, benzimidazalinyl, carbazolyl, 4aH-carbazolyl, carbolinyl, chromanyl, chromenyl, cinnolinyl, deca-hydroquinolinyl, 2H,6H-1,5,2-dithiazinyl, dihydrofuran[2,3-b]tetrahydrofuran, furanyl, furazanyl, imidazolidinyl, imidazolinyl, imidazolyl, 1H-indazolyl, indolinyl, indolizinyl, indolyl, 3H-indolyl, isobenzofuranyl, isochromanyl, isoindazolyl, isoindolinyl, isoindolyl, isoquinolinyl(benzimidazolyl), isothiazolyl, isoxazolyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, pyrimidinyl, phenanthridinyl, phenanthrolinyl, phenazinyl, phenothiazinyl, phenoxathiinyl, phenoxazinyl, phthalazinyl, piperazinyl, piperidinyl, pteridinyl, purinyl, pyranyl, pyrazinyl, pyroazolidinyl, pyrazolinyl, pyrazolyl, pyridazinyl, pyridooxazolyl, pyridoimidazolyl, pyridothiazolyl, pyridothiophenyl, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, 6H-1,2,5-thiadazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2,3-triazolyl, 1,2,3-triazolyl, 1,2,4-triazolyl, 1,2,5-triazolyl, 1,3,4-triazolyl or xanthenyl, and is unsubstituted or substituted, independently of each other, once, twice or three times, by G, R$^4$ is
—$(C_1-C_6)$-alkyl that is unsubstituted or substituted, once, twice or three times, by halogen, —$(C_3-C_6)$-cycloalkyl, phenyl, naphthyl, acridinyl, azetidinyl, benzimidazolyl, benzofuranyl, benzothiofuranyl, benzothiophenyl, benzoxazolyl, benzothiazolyl, benzotriazolyl, benzotetrazolyl, benzisoxazolyl, benzisothiazolyl, benzimidazalinyl, carbazolyl, 4aH-carbazolyl, carbolinyl, chromanyl, chromenyl, cinnolinyl, deca-hydroquinolinyl, 2H,6H-1,5,2-dithiazinyl, dihydrofuran[2,3-b]tetrahydrofuran, furanyl, furazanyl, imidazolidinyl, imidazolinyl, imidazolyl, 1H-indazolyl, indolinyl, indolizinyl, indolyl, 3H-indolyl, isobenzofuranyl, isochromanyl, isoindazolyl, isoindolinyl, isoindolyl, isoquinolinyl (benzimidazolyl), isothiazolyl, isoxazolyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, pyrimidinyl, phenanthridinyl, phenanthrolinyl, phenazinyl, phenothiazinyl, phenoxathiinyl, phenoxazinyl, phthalazinyl, piperazinyl, piperidinyl, pteridinyl, purinyl, pyranyl, pyrazinyl, pyroazolidinyl, pyrazolinyl, pyrazolyl, pyridazinyl, pyridooxazolyl, pyridoimidazolyl, pyridothiazolyl, pyridothiophenyl, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, 6H-1,2,5-thiadazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2,3-triazolyl, 1,2,3-triazolyl, 1,2,4-triazolyl, 1,2,5-triazolyl, 1,3,4-triazolyl or xanthenyl, and is unsubstituted or substituted, independently of each other, once, twice or three times, by G, —$(C_6-C_{14})$-aryl that is phenyl or naphthyl, or heteroaryl that is acridinyl, azetidinyl, benzimidazolyl, benzofuranyl, benzothiofuranyl, benzothiophenyl, benzoxazolyl, benzothiazolyl, benzotriazolyl, benzotetrazolyl, benzisoxazolyl, benzisothiazolyl, benzimidazalinyl, carbazolyl, 4aH-carbazolyl, carbolinyl, chromanyl, chromenyl, cinnolinyl, deca-hydroquinolinyl, 2H,6H-1,5,2-dithiazinyl, dihydrofuran[2,3-b]tetrahydrofuran, furanyl, furazanyl, imidazolidinyl, imidazolinyl, imidazolyl, 1H-indazolyl, indolinyl, indolizinyl, indolyl, 3H-indolyl, isobenzofuranyl, isochromanyl, isoindazolyl, isoindolinyl, isoindolyl, isoquinolinyl(benzimidazolyl), isothiazolyl, isoxazolyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, pyrimidinyl, phenanthridinyl, phenanthrolinyl, phenazinyl, phenothiazinyl, phenoxathiinyl, phenoxazinyl, phthalazinyl, piperazinyl, piperidinyl, pteridinyl, purinyl, pyranyl, pyrazinyl, pyroazolidinyl, pyrazolinyl, pyrazolyl, pyridazinyl, pyridooxazolyl, pyridoimidazolyl, pyridothiazolyl, pyridothiophenyl, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, 6H-1,2,5-thiadazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2,3-triazolyl, 1,2,3-triazolyl, 1,2,4-triazolyl, 1,2,5-triazolyl, 1,3,4-triazolyl or xanthenyl, and is unsubstituted or substituted, independently of each other, once, twice or three times, by G, $R^5$ is —$(C_1$-$C_6)$-alkyl that is unsubstituted or substituted, once, twice or three times, by —$(C_3$-$C_6)$-cycloalkyl, phenyl, naphthyl, acridinyl, azetidinyl, benzimidazolyl, benzofuranyl, benzothiofuranyl, benzothiophenyl, benzoxazolyl, benzothiazolyl, benzotriazolyl, benzotetrazolyl, benzisoxazolyl, benzisothiazolyl, benzimidazalinyl, carbazolyl, 4aH-carbazolyl, carbolinyl, chromanyl, chromenyl, cinnolinyl, deca-hydroquinolinyl, 2H,6H-1,5,2-dithiazinyl, dihydrofuran[2,3-b]tetrahydrofuran, furanyl, furazanyl, imidazolidinyl, imidazolinyl, imidazolyl, 1H-indazolyl, indolinyl, indolizinyl, indolyl, 3H-indolyl, isobenzofuranyl, isochromanyl, isoindazolyl, isoindolinyl, isoindolyl, isoquinolinyl (benzimidazolyl), isothiazolyl, isoxazolyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, pyrimidinyl, phenanthridinyl, phenanthrolinyl, phenazinyl, phenothiazinyl, phenoxathiinyl, phenoxazinyl, phthalazinyl, piperazinyl, piperidinyl, pteridinyl, purinyl, pyranyl, pyrazinyl, pyroazolidinyl, pyrazolinyl, pyrazolyl, pyridazinyl, pyridooxazolyl, pyridoimidazolyl, pyridothiazolyl, pyridothiophenyl, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, 6H-1,2,5-thiadazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2,3-triazolyl, 1,2,3-triazolyl, 1,2,4-triazolyl, 1,2,5-triazolyl, 1,3,4-triazolyl or xanthenyl, and is unsubstituted or substituted, independently of each other, once, twice or three times, by G, —$(C_6$-$C_{14})$-aryl that is phenyl or naphthyl, or heteroaryl that is acridinyl, azetidinyl, benzimidazolyl, benzofuranyl, benzothiofuranyl, benzothiophenyl, benzoxazolyl, benzothiazolyl, benzotriazolyl, benzotetrazolyl, benzisoxazolyl, benzisothiazolyl, benzimidazalinyl, carbazolyl, 4aH-carbazolyl, carbolinyl, chromanyl, chromenyl, cinnolinyl, deca-hydroquinolinyl, 2H,6H-1,5,2-dithiazinyl, dihydrofuran[2,3-b]tetrahydrofuran, furanyl, furazanyl, imidazolidinyl, imidazolinyl, imidazolyl, 1H-indazolyl, indolinyl, indolizinyl, indolyl, 3H-indolyl, isobenzofuranyl, isochromanyl, isoindazolyl, isoindolinyl, isoindolyl, isoquinolinyl (benzimidazolyl), isothiazolyl, isoxazolyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, pyrimidinyl, phenanthridinyl, phenanthrolinyl, phenazinyl, phenothiazinyl, phenoxathiinyl, phenoxazinyl, phthalazinyl, piperazinyl, piperidinyl, pteridinyl, purinyl, pyranyl, pyrazinyl, pyroazolidinyl, pyrazolinyl, pyrazolyl, pyridazinyl, pyridooxazolyl, pyridoimidazolyl, pyridothiazolyl, pyridothiophenyl, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, 6H-1,2,5-thiadazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2,3-triazolyl, 1,2,3-triazolyl, 1,2,4-triazolyl, 1,2,5-triazolyl, 1,3,4-triazolyl or xanthenyl, and is unsubstituted or substituted, independently of each other, once, twice or three times, by G, $R^6$ is —$(C_1$-$C_6)$-alkyl that is unsubstituted or substituted, once, twice or three times, by —$(C_3$-$C_6)$-cycloalkyl, phenyl, naphthyl, acridinyl, azetidinyl, benzimidazolyl, benzofuranyl, benzothiofuranyl, benzothiophenyl, benzoxazolyl, benzothiazolyl, benzotriazolyl, benzotetrazolyl, benzisoxazolyl, benzisothiazolyl, benzimidazalinyl, carbazolyl, 4aH-carbazolyl, carbolinyl, chromanyl, chromenyl, cinnolinyl, deca-hydroquinolinyl, 2H,6H-1,5,2-dithiazinyl, dihydrofuran[2,3-b]tetrahydrofuran, furanyl, furazanyl, imidazolidinyl, imidazolinyl, imidazolyl, 1H-indazolyl, indolinyl, indolizinyl, indolyl, 3H-indolyl, isobenzofuranyl, isochromanyl, isoindazolyl, isoindolinyl, isoindolyl, isoquinolinyl (benzimidazolyl), isothiazolyl, isoxazolyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, pyrimidinyl, phenanthridinyl, phenanthrolinyl, phenazinyl, phenothiazinyl, phenoxathiinyl, phenoxazinyl, phthalazinyl, piperazinyl, piperidinyl, pteridinyl, purinyl, pyranyl, pyrazinyl, pyroazolidinyl, pyrazolinyl, pyrazolyl, pyridazinyl, pyridooxazolyl, pyridoimidazolyl, pyridothiazolyl, pyridothiophenyl, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, 6H-1,2,5-thiadazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2,3-triazolyl, 1,2,3-triazolyl, 1,2,4-triazolyl, 1,2,5-triazolyl, 1,3,4-triazolyl or xanthenyl, and is unsubstituted or substituted, independently of each other, once, twice or three times, by G, —$(C_6$-$C_{14})$-aryl is phenyl or naphthyl, or heteroaryl that is acridinyl, azetidinyl, benzimidazolyl, benzofuranyl, benzothiofuranyl, benzothiophenyl, benzoxazolyl, benzothiazolyl, benzotriazolyl, benzotetrazolyl, benzisoxazolyl, benzisothiazolyl, benzimidazalinyl, carbazolyl, 4aH-carbazolyl, carbolinyl, chromanyl, chromenyl, cinnolinyl, deca-hydroquinolinyl, 2H,6H-1,5,2-dithiazinyl, dihydrofuran[2,3-b]tetrahydrofuran, furanyl, furazanyl, imidazolidinyl, imidazolinyl, imidazolyl, 1H-indazolyl, indolinyl, indolizinyl, indolyl, 3H-indolyl, isobenzofuranyl, isochromanyl, isoindazolyl, isoindolinyl, isoindolyl, isoquinolinyl(benzimidazolyl), isothiazolyl, isoxazolyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, pyrimidinyl, phenanthridinyl, phenanthrolinyl, phenazinyl, phenothiazinyl, phenoxathiinyl, phenoxazinyl, phthalazinyl, piperazinyl, piperidinyl, pteridinyl, purinyl, pyranyl, pyrazinyl, pyroazolidinyl, pyrazolinyl, pyrazolyl, pyridazinyl, pyridooxazolyl, pyridoimidazolyl, pyridothiazolyl, pyridothiophenyl, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, 6H-1,2,5-thiadazinyl, 1,2,3- thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2,3-triazolyl, 1,2,3-triazolyl, 1,2,4-triazolyl, 1,2,5-triazolyl, 1,3,4-triazolyl or xanthenyl, and is unsubstituted or substituted, independently of each other, once, twice or three times, by G, and $R^1$ is —$(C_1$-$C_6)$-alkyl that is unsubstituted or substituted, once, twice or three times, by —$(C_3$-$C_6)$-cycloalkyl, phenyl, naphthyl, acridinyl, azetidinyl, benzimidazolyl, benzofuranyl, benzothiofuranyl, benzothiophenyl, benzoxazolyl, benzothiazolyl, benzotriazolyl, benzotetrazolyl, benzisoxazolyl, benzisothiazolyl, benzimidazalinyl, carbazolyl, 4aH-carbazolyl, carbolinyl, chromanyl, chromenyl, cinnolinyl, deca-hydroquinolinyl, 2H,6H-1,5,2-dithiazinyl, dihydrofuran[2,3-b]tetrahydrofuran, furanyl, furazanyl, imidazolidinyl, imidazolinyl, imidazolyl, 1H-indazolyl, indolinyl, indolizinyl, indolyl, 3H-indolyl, isobenzofuranyl, isochromanyl, isoindazolyl, isoindolinyl, isoindolyl, isoquinolinyl (benzimidazolyl), isothiazolyl, isoxazolyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, pyrimidinyl, phenanthridinyl, phenanthrolinyl, phenazinyl, phenothiazinyl, phenoxathiinyl, phenoxazinyl, phthalazinyl, piperazinyl, piperidinyl, pteridinyl, purinyl, pyranyl, pyrazinyl, pyroazolidinyl, pyrazolinyl, pyrazolyl, pyridazinyl, pyridooxazolyl, pyridoimidazolyl, pyridothiazolyl, pyridothiophenyl, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, 6H-1,2,5-thiadazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2,3-triazolyl, 1,2,3-triazolyl, 1,2,4-triazolyl, 1,2,5-triazolyl, 1,3,4-triazolyl or xanthenyl, and is unsubstituted or substituted, independently of each other, once, twice or three times, by G.

Another embodiment of the invention relates to the compound of formula I wherein B, D and E are identical or different and are, independently of each other, —$(C_0$-$C_2)$-alkylene,
—$C_2$-alkenylene,
—$S(O)_2$—,
—NH—,
—NH—C(O)—,
—C(O)—NH—,
—NH—C(O)—NH—,
—O—, or
—C(O)—, $ring^1$, $ring^2$ or $ring^3$ are —$(C_6$-$C_{14})$-aryl that is phenyl or naphthyl that is unsubstituted or substituted, independently of each other, once, twice or three times, by G, or 5- or 6-membered aromatic heteroaryl ring that is dihydrofuranyl, furanyl, morpholinyl, piperazinyl, piperidinyl, pyridinyl, pyrimidinyl, pyrrolyl, thiazolyl or thiophenyl, and is unsubstituted or substituted, independently of each other, once, twice or three times, by G, $ring^4$ is —$(C_6$-$C_{14})$-aryl that is phenyl or naphthyl and is unsubstituted or substituted, independently of each other, once, twice or three times, by G, 5- or 6-membered aromatic heteroaryl ring is dihydrofuranyl, furanyl, morpholinyl, piperazinyl, piperidinyl, pyridinyl, pyrimidinyl, pyrrolyl, thiazolyl or thiophenyl and is unsubstituted or substituted, independently of each other, once, twice or three times, by G, heteroaryl that is benzofuranyl, benzothiophenyl, dihydrofuranyl, furanyl, morpholinyl, piperazinyl, piperidinyl, pyridinyl, pyridothiophenyl, pyrimidinyl, pyrrolyl, thiazolyl or thiophenyl, and is unsubstituted or substituted, independently of each other, once, twice or three times, by G, or azaheterocyclyl selected from the group consisting of

 and 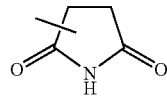

that is unsubstituted or substituted, independently of each other, once, twice or three times, by G, G is halogen that is Br, Cl, I or F, or
—$S(O)_p$—$R^4$ that is —$S(O)_2$—$R^4$, $R^4$ is hydrogen,
—$(C_1$-$C_4)$-alkyl that is unsubstituted or substituted, once, twice or three times, by Br, Cl, F, —$C_3$-cycloalkyl, phenyl, naphthyl, or heteroaryl that is benzofuranyl, benzothiophenyl, dihydrofuranyl, furanyl, morpholinyl, piperazinyl, piperidinyl, pyridinyl, pyridothiophenyl, pyrimidinyl, pyrrolyl, thiazolyl or thiophenyl, and is unsubstituted or substituted, independently of each other, once, twice or three times, by G,
phenyl or naphthyl,
heteroaryl that is benzofuranyl, benzothiophenyl, dihydrofuranyl, furanyl, morpholinyl, piperazinyl, piperidinyl, pyridinyl, pyridothiophenyl, pyrimidinyl, pyrrolyl, thiazolyl or thiophenyl and are unsubstituted or substituted, independently of each other, once, twice or three times, by G,
—C(O)—O—$R^5$, or
—C(O)—NH—$R^6$, $R^5$ is —$(C_1$-$C_4)$-alkyl that is unsubstituted or substituted, once or twice, by —$C_3$-cycloalkyl, phenyl, naphthyl or heteroaryl that is benzofuranyl, benzothiophenyl, dihydrofuranyl, furanyl, morpholinyl, piperazinyl, piperidinyl, pyridinyl, pyridothiophenyl, pyrimidinyl, pyrrolyl, thiazolyl or thiophenyl, and is unsubstituted or substituted, independently of each other, once, twice or three times, by G,
phenyl or naphthyl, or
heteroaryl that is benzofuranyl, benzothiophenyl, dihydrofuranyl, furanyl, morpholinyl, piperazinyl, piperidinyl, pyridinyl, pyridothiophenyl, pyrimidinyl, pyrrolyl, thiazolyl or thiophenyl, and is substituted, independently of each other, once, twice or three times, by G, $R^6$ is —$(C_1$-$C_4)$-alkyl, in which alkyl is unsubstituted or substituted, once or twice, by —$C_3$-cycloalkyl, phenyl, naphthyl or heteroaryl that is benzofuranyl, benzothiophenyl, dihydrofuranyl, furanyl, morpholinyl, piperazinyl, piperidinyl, pyridinyl, pyridothiophenyl, pyrimidinyl, pyrrolyl, thiazolyl or thiophenyl, and is unsubstituted or substituted, independently of each other, once, twice or three times, by G, phenyl or naphthyl, or heteroaryl that is benzofuranyl, benzothiophenyl, dihydrofuranyl, furanyl, morpholinyl, piperazinyl, piperidinyl, pyridinyl, pyridothiophenyl, pyrimidinyl, pyrrolyl, thiazolyl or thiophenyl, and is substituted, independently of each other, once, twice or three times, by G, $X_1$ and $X_2$ are hydrogen, $n^1$ and $n^2$ are —$(CH_2)$—, or $n^1$ is —$(CH_2)_2$— and $n^2$ is —$(CH_2)$—, $R^1$ is hydrogen, and $R^2$ and $R^3$ are hydrogen.

Preference is given to pyridyl; such as 2-pyridyl, 3-pyridyl or 4-pyridyl; pyrrolyl; such as 2-pyrrolyl and 3-pyrrolyl; furyl; such as 2-furyl and 3-furyl; thiophenyl, thienyl; such as 2-thienyl and 3-thienyl; imidazolyl, pyrazolyl, oxazolyl, isoxazolyl, thiazolyl, isothiazolyl, tetrazolyl, pyridazinyl, pyrazinyl, pyrimidinyl, indolyl, isoindolyl, benzofuranyl, benzothiophenyl, 1,3-benzodioxolyl, indazolyl, benzimidazolyl, benzoxazolyl, benzothiazolyl, quinolinyl, isoquinolinyl, chromanyl, isochromanyl, cinnolinyl, quinazolinyl, quinoxalinyl, phthalazinyl, pyridoimidazolyl, pyridopyridinyl, pyridopyrimidinyl, purinyl and pteridinyl.

Another particular embodiment of the invention is a process for the preparation of the compound according to formula I, comprising a) reacting a compound of formula IV,

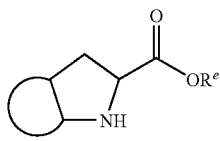

(IV)

wherein $R^e$ is hydrogen or an ester protecting group, with a compound of formula V, $R^z$—$SO_2$-A-ring$^1$-B-ring$^2$-D-ring$^3$-E-ring$^4$ (V)

in which A, B, D, E and ring$^1$, ring$^2$, ring$^3$ and ring$^4$ are defined as in the compound of formula I, and wherein $R^z$ is a chlorine atom, imidazolyl or OH, in the presence of a base, or after silylation with a suitable silylating agent, to give a compound of formula VI,

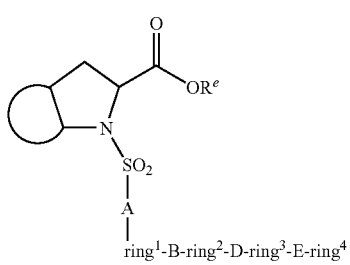

(VI)

wherein A, B, D, E, $R^e$ and ring$^1$, ring$^2$, ring$^3$ and ring$^4$ are as defined above, and b) where $R^e$ is the ester protecting group, reacting a compound of formula VI, which has been prepared in accordance with step a), with a solution of an alkali such as NaOH or LiOH, and then treating with acid, to give the carboxylic acid of formula VII, with modifications in one of the side chains of ring$^1$-ring$^4$ also having previously been carried out, where appropriate,

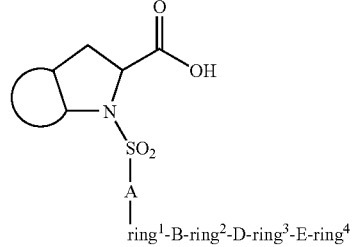

(VII)

and then converting this compound into the compound of formula I wherein X is NH—OH, and c) optionally separating the compound of formula I, which has been prepared in accordance with steps a) or b) into an individual enantiomer by means of salt formation with an enantiomerically pure acid or base, chromatography on a chiral stationary phase or derivatization using a chiral, enantiomerically pure compound, such as an amino acid, separation of the resulting derivatized diastereomers and elimination of the chiral auxiliary derivatization group, or d) optionally isolating the compound of formula I, which has been prepared in accordance with steps b) or c), in free form or, when an acidic or basic group is present, converting it into a corresponding physiologically tolerated salt.

Compounds such as those of formulae IV to VII are only exemplary compounds; in accordance with formula I it is also possible to configure four-ring, six-ring and seven-ring compounds instead of the five-ring compound.

The groups that are used for protecting esters in Protective Groups in Organic Synthesis, T. H. Greene, P. G. M. Wuts, Wiley-Interscience, 1991, can be employed as the ester protecting group $R^e$. Examples of preferred ester protecting groups are methyl, ethyl, isopropyl, tert-butyl or benzyl.

The starting compounds and reagents that are used can either be prepared using known methods or are commercially available.

The reactions take place as depicted, for example, in WO 97/18194. The reaction in accordance with process step a) takes place in the presence of a base such as KOH, NaOH, LiOH, N,O-bis(trimethylsilyl)acetamide (BSA), N-methylmorpholine (NMM), N-ethylmorpholine (NEM), triethylamine (TEA), diisopropylethylamine (DIPEA), pyridine, collidine, imidazole or sodium carbonate in solvents such as tetrahydrofuran (THF), dimethylformamide (DMF), dimethylacetamide, dioxane, acetonitrile, toluene, chloroform or methylene chloride, or else in the presence of water.

Modifications in the side chain F means that, for example, a nitro group is hydrogenated using the metal catalyst Pd/C or reacted with $SnCl_2$ or Zn under standard conditions and the resulting amino group can then be subjected to further modification, for example by reacting it with carbonyl chlorides, sulfonyl chlorides, chloroformic esters, isocyanates, isothiocyanates, or other reactive or activatable reagents, in order to arrive at the precursors of the novel compounds of formula I. For this case, it is frequently advantageous if $R^e$ is an ester in compound VI since side reactions are to be expected when the carboxylic acid is unprotected.

Provided it arises as a mixture of diastereomers or enantiomers, or accrues in the chosen synthesis as their mixtures, the compound of formula I is separated, in process step c), into the pure stereoisomers either by means of chromatography on an optionally chiral support material or, provided the racemic compound of formula I is capable of salt formation, by means of fractional crystallization of the diastereomeric salts which have been formed using an optically active base or acid as auxiliary substance. Examples of suitable chiral stationary phases for the thin-layer or column chromatographic separation of enantiomers are modified silica gel supports (what are termed Pirkle phases) and also high molecular weight carbohydrates, such as triacetyl cellulose. Following appropriate derivatization, which is known to the skilled person, gas-chromatographic methods on chiral stationary phases can also be used for analytical purposes. In order to separate the enantiomers of the racemic carboxylic acids, the diastereomeric salts, which differ in solubility, are formed using an optically active, as a rule commercially available, base such as (−)-nicotine, (+)- and (−)-phenylethylamine, quinine bases, L-lysine or L- and D-arginine, the more sparingly soluble component is isolated as a solid, the more readily soluble diastereomer is separated out from the mother liquor, and the pure enantiomers are isolated from the diastereomer salts which have been obtained in this way. The racemic compounds of the formula I which contain a basic group, such as amino group, can, in what is in principle the same manner, be converted into the pure enantiomers using optically active acids, such as (+)-camphor-10-sulfonic acid, D- and L-tartaric acid, D- and L-lactic acid and (+) and (−)-mandelic acid. Chiral compounds which contain alcohol or amine functions can also be converted into the corresponding esters or amides using appropriately activated or optionally N-protected enantiomerically pure amino acids or, conversely, chiral carboxylic acids can be converted into the amides using carboxyl-protected enantiomerically pure amino acids or into the corresponding chiral esters using enantiomerically pure hydroxyl carboxylic acids such as lactic acid. The chirality of the amino acid or alcohol radical which has been introduced in enantiomerically pure form can then be used for separating the isomers by the diastereomers, which are now present, by means of crystallization or chromatography on suitable stationary phases and, after that, using suitable methods to once again eliminate the entrained chiral molecule moiety.

Acidic or basic products of the compound of the formula I may be present in the form of their salts or in free form. Preference is given to pharmacologically tolerated salts, e.g. alkali metal salts or alkaline earth metal salts or hydrochlorides, hydrobromides, sulfates, hemisulfates, all possible phosphates and also salts of the amino acids, natural bases or carboxylic acids.

Physiologically tolerated salts are prepared according to process step d) in a manner known per se from compounds of the formula I, including their stereoisomeric forms, which are capable of salt formation. The compounds of formula I form stable alkali metal salts, alkaline earth metal salts or optionally substituted ammonium salts with basic reagents such as hydroxides, carbonates, hydrogen carbonates, alkoxides and ammonia or organic bases, for example trimethylamine or triethylamine, ethanolamine, diethanolamine or triethanolamine, trometamol or else basic amino acids, for example lysine, ornithine or arginine. Insofar as the compounds of formula I possess basic groups, stable acid addition salts can also be prepared using strong acids. Both inorganic and organic acids, such as hydrochloric acid, hydrobromic acid, sulfuric acid, phosphoric acid, methanesulfonic acid, benzenesulfonic acid, p-toluenesulfonic acid, 4-bromobenzenesulfonic acid, cyclohexylamidosulfonic acid, trifluoromethylsulfonic acid, acetic acid, oxalic acid, tartaric acid, succinic acid glycerol phosphoric acid, lactic acid, malic acid, adipic acid, citric acid, fumaric acid, maleic acid, gluconic acid, glucuronic acid and trifluoroacetic acid are suitable for this purpose.

The invention also relates to a pharmaceutical preparation comprising a pharmaceutically effective amount of at least one compound of formula I and/or of a physiologically tolerated salt of the compound of formula I and/or an optionally stereoisomeric form of the compound of formula I, together with a pharmaceutically suitable and physiologically tolerated carrier substance, additive and/or other active compounds and auxiliary substances.

On account of their pharmacological properties, compounds according to the invention are suitable for the selective prophylaxis and therapy of all those diseases whose course involves an increase in the activity of the metalloproteinases. These diseases include degenerative joint diseases, such as osteoarthroses, spondyloses, cartilage loss following joint trauma or a relatively long period of joint immobilization following meniscus injuries or patella injuries or ligament rupture. They also include diseases of the connective tissue such as collagenoses, periodontal diseases, wound healing disturbances and chronic diseases of the locomotory apparatus, such as inflammatory, immunologically-determined or metabolism-determined acute and chronic arthritides, arthropathies, myalgias and disturbances in bone metabolism. In addition, the compound of formula I is suitable for treating ulceration, atherosclerosis and stenoses. The compound of formula I is furthermore suitable for treating inflammations, cancer diseases, tumor metastasis formation, cachexia, anorexia, heart failure and septic shock. The compound is also suitable for the prophylaxis of myocardial and cerebral infarcts.

The pharmaceutical according to the invention can be administered by means of oral, inhalative, rectal or transdermal administration or by means of subcutaneous, intraarticular, intraperitoneal or intravenous injection. Oral administration is preferred.

The invention also relates to a process for producing a pharmaceutical, in which process at least one compound of formula I is brought, together with a pharmaceutically suitable and physiologically tolerated excipient and, where appropriate, other suitable active compounds, additives or auxiliary substances, into a suitable form for administration.

Examples of suitable solid or galenic preparation forms are granules, powders, sugar-coated tablets, tablets, (micro)capsules, suppositories, syrups, juices, suspensions, emulsions, drops or injectable solutions, and also preparations involving a protracted release of active compound, in the production of which customary adjuvants such as carrier substances, disintegrants, binders, coating agents, swelling agents, glidants, lubricants, flavorings, sweeteners and solubilizers are used. Frequently employed auxiliary substances which may be mentioned are magnesium carbonate, titanium dioxide, lactose, mannitol and other sugars, talc, milk protein, gelatin, starch, cellulose and its derivatives, animal and vegetable oils, such as cod liver oil, sunflower oil, peanut oil or sesame oil, polyethylene glycol and solvents, such as sterile water and monohydric or polyhydric alcohols such as glycerol.

The pharmaceutical preparations are preferably produced and administered in dosage units, with each unit containing, as the active constituent, a defined dose of the novel compound of formula I. In the case of solid dose units, such as tablets, capsules, sugar-coated tablets or suppositories, this dose can be up to about 1,000 mg, preferably, however, from about 50 to 300 mg, while it can be up to about 300 mg, preferably, however, from about 10 to 100 mg, in the case of injection solutions in ampoule form.

Depending on the activity of the compound of formula I, daily doses of from about 20 mg to 1,000 mg of active compound, preferably of from about 100 mg to 500 mg, are indicated for treating an adult patient of about 70 kg in weight. However, higher or lower daily doses may also possibly be appropriate. The daily dose may be administered either by means of a once-only administration in the form of a single dosage unit or of several smaller dosage units or else by means of the multiple administration of subdivided doses at defined intervals.

The starting materials and intermediates may be prepared by the application or adaptation of known methods, or their obvious chemical equivalents.

The compounds of the invention, their methods or preparation and their biological activity will appear more clearly from the examination of the following examples which are presented as an illustration only and are not to be considered as limiting the invention in its scope.

EXAMPLES

As a rule, end products are determined by means of mass-spectroscopic methods (FAB MS, ESI MS) and $^1$H NMR (400 MHz, in DMSO-D6); the main peak or the two main peaks is/are given in each case. Temperatures are given in degrees centigrade; RT denotes room temperature (from 22° C. to 26° C.). Abbreviations that are used are either explained or conform to the customary conventions.

The invention is explained in more detail below with the aid of examples.

1-Arylsulfonyloctahydrocyclopenta[b]pyrrole-2-carboxylic acid

General Directions 1:

The carboxylic acid (6.45 mmol) is dissolved in 20 ml of dimethylformamide (DMF), after which 3 equivalents of a 3N solution of NaOH (6.45 ml) are added at 0° C. After 10 min, a solution of the arylsulfonyl chloride (1.1 equivalents, 7.1 mmol) in from 10 to 15 ml of DMF was slowly added dropwise; after the mixture had reached room temperature, it was stirred for at most a further 12 hours (h) at temperatures of between 20° C. and 80° C. and the solvent was removed under reduced pressure. The crude product was purified chromatographically.

Examples:

Compound No. 4: 1-[4-(1,1-Dimethylpropyl)benzenesulfonyl]octahydro-cyclopenta[b]pyrrole-2-carboxylic acid 1 g of octahydrocyclopenta[b]pyrrole-2-carboxylic acid (6.45 mmol) was dissolved in 20 ml of DMF, after which 3 equivalents of a 3 N solution of NaOH (6.45 ml) were added at 0° C. After 10 minutes (min), a solution of 1.75 g of 4-(1,1-dimethylpropylbenzenesulfonyl chloride (1.1 equivalents, 7.1 mmol) in 12 ml of DMF was slowly added dropwise; after it had reached room temperature (RT), the mixture was stirred at 40° C. for a further 6 h and, after that, the solvent was removed under reduced pressure. The crude product was purified chromatographically.

Compound No. 20: 1-(4-Acetylbenzenesulfonyl)octahydrocyclopenta[b]pyrrole-2-carboxylic acid 1 g of octahydrocyclopenta[b]pyrrole-2-carboxylic acid (6.45 mmol) was dissolved in 20 ml of DMF, after which 3 equivalents of a 3N solution of NaOH (6.45 ml) were added at 0° C. After 10 min, a solution of 1.55 g of 4-acetylbenzenesulfonyl chloride (1.1 equivalents, 7.1 mmol) in 8 ml of DMF was slowly added dropwise; after it had reached RT, the mixture was stirred at 40° C. for a further 6 h and, after that, the solvent was removed under reduced pressure. The crude product was purified chromatographically.

1-Arylsulfonyloctahydrocyclopenta[b]pyrrole-2-carboxylic acid hydroxyamide

General directions 2:

The sulfonated carboxylic acid was dissolved in 10 ml of DMF, after which 1.1 equivalents of ethyl chloroformate, 2.2 equivalents of N-ethylmorpholine and 3 equivalents of trimethylsilylhydroxylamine were added. After the mixture had been heated at 80° C. for at least 4 h, the solvent was removed under reduced pressure and the crude product was purified using chromatographic methods.

Examples

Compound No. 50: 1-(Naphthaline-1-sulfonyl)octahydrocyclopenta[b]pyrrole-2-carboxylic acid hydroxyamide 200 mg (0.56 mmol) of 1-(naphthaline-1-sulfonyl)octahydrocyclopenta[b]pyrrole-2-carboxylic acid were dissolved in 10 ml of DMF, after which 0.61 mmol of ethyl chloroformate, 1.23 mmol of N-ethylmorpholine and 1.68 mmol of trimethylsilylhydroxylamine were added. After the mixture had been heated at 80° C. for 6 h, the solvent was removed under reduced pressure and the crude product was purified using chromatographic methods.

Compound No. 52: 1-(4-Methanesulfonylbenzenesulfonyl)octahydrocyclopenta[b]pyrrole-2-carboxylic acid hydroxyamide 200 mg (0.55 mmol) of 1-(4-methanesulfonylbenzenesulfonyl)octahydrocyclopenta-[b]pyrrole-2-carboxylic acid were dissolved in 10 ml of DMF, after which 0.60 mmol of ethyl chloroformate, 1.22 mmol of N-ethylmorpholine and 1.67 mmol of trimethylsilylhydroxylamine were added. After the mixture had been heated at 80° C. for 4 h, the solvent was removed under reduced pressure and the crude product was purified using chromatographic methods.

Special Directions:

Compound No. 27: 1-(4'-Aminobiphenyl-4-sulfonyl)octahydrocyclopenta[b]pyrrole-2-carboxylic acid 1 g of 1-(4'-nitrobiphenyl-4-sulfonyl)octahydrocyclopenta[b]pyrrole-2-carboxylic acid (27) was dissolved in 15 ml of DMF, after which 0.1 g of hydrogenation catalyst (10% Pd on active charcoal) was added and the starting compound was quantitatively hydrogenated within 2 h. After the solvent had been removed, the crude product was purified chromatographically.

Compound No. 37: 1-(4-Aminobenzenesulfonyl) octahydrocyclopenta[b]pyrrole-2-carboxylic acid 1 g of 1-(4-nitrobenzenesulfonyl)octahydrocyclopenta[b]pyrrole-2-carboxylic acid (14) was dissolved in 15 ml of DMF, after which 0.1 g of hydrogenation catalyst (10% Pd on active charcoal) was added and the starting compound was quantitatively hydrogenated within 2 h. After the solvent had been removed, the crude product was purified chromatographically.

Compound No. 22: 1-(4'-Isopropoxycarbonylaminobiphenyl-4-sulfonyl)octahydro-cyclopenta[b]pyrrole-2-carboxylic acid 500 mg (1.30 mmol) of 1-(4'-aminobiphenyl-4-sulfonyl)octahydrocyclopenta[b]pyrrole-2-carboxylic acid were dissolved in 3 ml of DMF, after which the solution was cooled down to 0° C. in an ice bath and 2.6 mmol of pyridine were added. After the mixture had been stirred at 0° C. for 15 min, 2 mmol of isopropyl chloroformate in 3 ml of DMF were added. The reaction solution was then stirred at RT for a further 2 h. The crude product was purified using chromatographic methods.

Compound No. 32: 1-(4'-Cyclopropylmethoxycarbonylaminobiphenyl-4-sulfonyl)-octahydrocyclopenta[b]pyrrole-2-carboxylic acid 500 mg (1.30 mmol) of 1-(4'-aminobiphenyl-4-sulfonyl)octahydrocyclopenta[b]pyrrole-2-carboxylic acid were dissolved in 3 ml of DMF, after which the solution was cooled down to 0° C. in an ice bath and 2.6 mmol of pyridine were added. After the mixture had been stirred at 0° C. for 15 min, 2 mmol of cyclopropylmethyl chloroformate in 3 ml of DMF were added. The reaction solution was then stirred at RT for a further 6 h. The crude product was purified using chromatographic methods.

Compound No. 23: 1-(4'-Methanesulfonylaminobiphenyl-4-sulfonyl)octahydro-cyclopenta[b]pyrrole-2-carboxylic acid 500 mg (1.30 mmol) of 1-(4'-aminobiphenyl-4-sulfonyl)octahydrocyclopenta[b]pyrrole-2-carboxylic acid were dissolved in 3 ml of DMF, after which the solution was cooled down to 0° C. in an ice bath and 2.6 mmol of pyridine were added. After the mixture had been stirred at 0° C. for 15 min, 1.40 mmol of methanesulfonyl chloride in 3 ml of DMF were added. The reaction solution was then stirred at room temperature for a further 6 h. The crude product was purified using chromatographic methods.

Compound No. 25: 1-(4'-Benzenesulfonylaminobiphenyl-4-sulfonyl)octahydro-cyclopenta[b]pyrrole-2-carboxylic acid 500 mg (1.30 mmol) of 1-(4'-aminobiphenyl-4-sulfonyl)octahydrocyclopenta[b]pyrrole-2-carboxylic acid were dissolved in 3 ml of DMF, after which the solution was cooled down to 0° C. in an ice bath and 2.6 mmol of pyridine were added. After the mixture had been stirred at 0° C. for 15 min, 1.5 mmol of benzenesulfonyl chloride in 6 ml of DMF were added. The reaction solution was then stirred at RT for a further 12 h. The crude product was purified using chromatographic methods.

Compound No. 24: 1-(4'-Benzoylaminobiphenyl-4-sulfonyl)octahydro-cyclopenta[b]pyrrole-2-carboxylic acid 500 mg (1.30 mmol) of 1-(4'-aminobiphenyl-4-sulfonyl)octahydrocyclopenta[b]pyrrole-2-carboxylic acid were dissolved in 3 ml of DMF, after which the solution was cooled down to 0° C. in an ice bath and 2.6 mmol of pyridine were added. After the mixture had been stirred at 0° C. for 15 min, 1.8 mmol of benzoyl chloride in 3 ml of DMF were added. The reaction solution was then stirred at RT for a further 20 h. The crude product was purified using chromatographic methods.

Compound No. 26: 1-[4'-(3-Phenylureido)biphenyl-4-sulfonyl]octahydro-cyclopenta[b]pyrrole-2-carboxylic acid 500 mg (1.30 mmol) of 1-(4'-aminobiphenyl-4-sulfonyl)octahydrocyclopenta[b]pyrrole-2-carboxylic acid were dissolved in 3 ml of DMF, after which the solution was cooled down to 0° C. in an ice bath and 1.4 mmol of phenylisocyanate were added. The reaction solution was then stirred at RT for a further 4 h. The crude product was purified using chromatographic methods.

Preparation Examples

| No. | Structure | | MS (ESI+) | NMR |
|---|---|---|---|---|
| 1 | (structure) | Chiral | 399.92 400.10 | 1.4-1.85: m, 6 H; 1.9: m, 1 H; 2.35: m, 1 H; 2.55: m, 1 H; 2.7: s, 3 H; 4.0: m, 1 H; 4.2: m, 1 H; 7.6: d, 1 H;(.1: m, 2 H; 12.1, bs, 1 H |
| 2 | (structure) | | 373.45 374.08 | 1.3-1.9: m, 8 H; 2.15: m, 1 H; 3.95: m, 1 H; 3.3: s, 3 H; 4.2: m, 1 H; 8.1: d,2 H; 8.2: d, 2 H; 12.5: bs, 1 H |

-continued

| No. | Structure | MS (ESI+) | NMR |
|---|---|---|---|
| 3 | Chiral | 374.26 374.06 | 1.4-1.9: m, 7 H; 2.15: m, 1 H; 2.45: m, 1 H; 3.9: m, 1 H; 4.1: m, 1 H; 7.75: d, 2 H; 7.85: d, 2 H 13.0: bs, 1 H |
| 4 | Chiral | 365.9 366.19 | 0.6: t, 3 H; 1.3: s, 6 H; 1.35-1.8: m, 8 H; 1.9: m, 1 H; 2.1: m, 1 H; 2.4: m, 1 H; 3.85: m, 1 H; 4.0: m, 1 H; 7.55: d, 2 H; 7.75: d, 2 H; 12.8: bs, 1 H |
| 5 | Chiral | 351.47 352.15 | 1.45: s, 9 H; 1.5-1.8: m, 6 H; 1.9: m, 1 H; 2.15: m, 1 H; 2.45: m, 1 H; 3.85: m, 1 H; 4.05: m, 1 H; 7.6: d, 2 H; 7.85: d, 2 H; 12.5: s, 1 H |
| 6 | Chiral | 309.39 310.22 | 1.35: m, 2 H; 1.7: m, 5 H; 2.3: m, 1 H; 2.65: m, 1 H; 4.15: m, 2 H; 4.5: m, 2 H; 7.4: m, 5 H |
| 7 | Chiral | 441.55 442.11 | 1.3-1.9: m, 7 H; 2.2: m, 1 H; 2.55: m, 1 H; 4.0: m, 1 H; 4.2: m, 1 H; 7.6: m, 2 H; 7.8: m, 2 H; 7.95: m, 1 H; 8.05: m, 2 H; 13.0: bs, 1 H |
| 8 | Chiral | 352.01 353.14 | 1.3-1.8: m, 6 H; 1.9: m, 1 H; 2.1: s, 3 H; 2.15: m, 1 H; 2.45: m, 1 H; 3.85: m, 1 H; 4.0: m, 1 H; 7.8: m, 4 H; 10.9: s, 1 H |
| 9 | Chiral | 345.42 346.10 | 1.3-1.8: m, 6 H; 1.9: m, 1 H; 2.1: m, 1 H; 2.4: m, 1 H; 3.95: m, 1 H; 4.2: m, 1 H; 7.7: m, 2 H; 7.9: d, 1 H; 8.05: d, 1 H; 8.15: d, 1 H; 8.2: d, 1 H; 8.5: s, 1 H; 12.8: bs, 1 H |
| 10 | Chiral | 446.91 447.11 | 1.3-1.8: m, 6 H; 1.9: m, 1 H; 2.15: m, 1 H; 2.45: m, 1 H; 3.9: m, 1 H; 4.1: m, 1 H; 7.2: d, 1 H; 7.4: d, 2 H; 7.6: d, 1 H; 7.75: m, 2 H; 7.9: d, 2 H |

-continued

| No. | Structure | | MS (ESI+) | NMR |
|---|---|---|---|---|
| 11 | 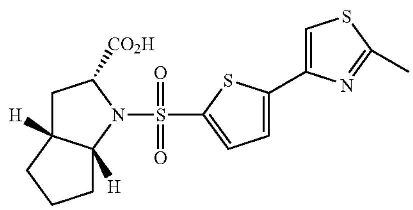 | Chiral | 398.52<br>399.02 | 1.3-1.8: m, 6 H; 1.95: m, 1 H; 2.2: m, 1 H; 2.5: m, 1 H; 2.7: s, 3 H; 3.95: m, 1 H; 4.05: m, 1 H; 7.65: s, 2 H; 8.1: s, 1 H |
| 12 | 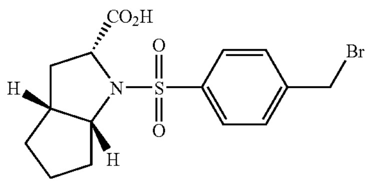 | Chiral | 388.28<br>388.04 | 1.3-1.8: m, 6 H; 1.9: m, 1 H; 2.1: m, 1 H; 2.45: m, 1 H; 3.9: m, 1 H; 4.1: m, 1 H; 4.4: s, 2 H; 7.7: d, 2 H; 7.85: d, 2 H |
| 13 | 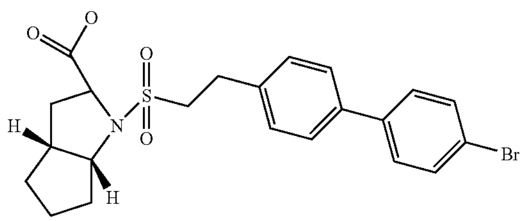 | | 478.41<br>480.04 | 1.3-1.9: m, 7 H; 2.4: m, 1 H; 2.7: m, 1 H; 3.05: t, 2 H; 3.45: 2 H; 4.25: m, 1 H; 4.35: m, 1 H; 7.35: m, 2 H; 7.65: m, 6 H |
| 14 | 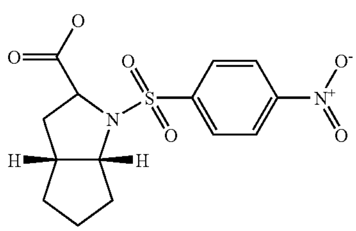 | | 340.36<br>341.04 | 1.3-1.9: m, 7 H; 2.1: m, 1 H; 2.45: m, 1 H; 3.9: m, 1 H; 4.2: m, 1 H; 8.1: d, 2 H; 8.4: d, 2 H |
| 15 | 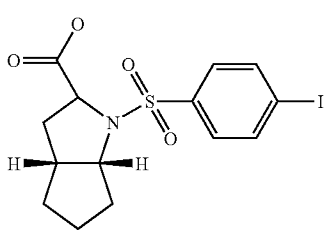 | | 421.26<br>421.97 | 1.3-1.8: m, 6 H; 1.9: m, 1 H; 2.1: m, 1 H; 2.45: m, 1 H; 3.8: m, 1 H; 4.05: m, 1 H; 7.55: d, 1 H; 8.05: d, 1 H |
| 16 | 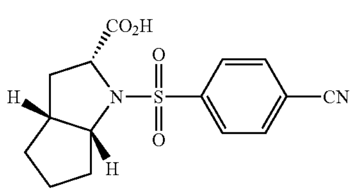 | Chiral | 320.37<br>321.10 | 1.3-1.9: m, 7 H; 2.2: m, 1 H; 2.45: m, 1 H; 3.95: m, 1 H; 4.2: m, 1 H; 8.0: d, 2 H; 8.1: d, 2 H; 12.8: s, 1 H |
| 17 | 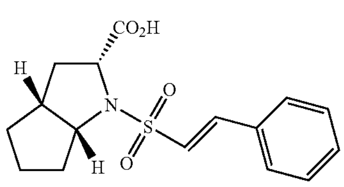 | Chiral | 321.39<br>322.02 | 1.35-1.8: m, 6 H; 1.95: m, 1 H; 2.4: m, 1 H; 2.65: m, 1 H; 4.05: m, 1 H; 4.2: m, 1 H; 7.4: s, 2 H; 7.45: m, 3 H; 7.7: m, 2 H |

-continued

| No. | Structure | | MS (ESI+) | NMR |
|---|---|---|---|---|
| 18 | 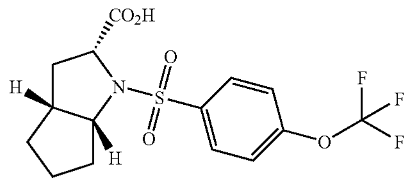 | | 379.36 <br> 379.97 | 1.3-1.9: m, 7 H; 2.15: m, 1 H; 2.5: m, 1 H; 3.9: m, 1 H; 4.1: m, 1 H; 7.6: d, 2 H; 8.0: d, 2 H; 12.8: s, 1 H |
| 19 | 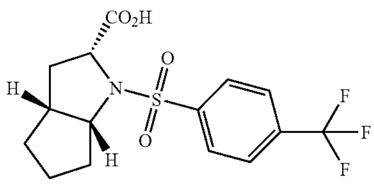 | Chiral | 363.36 <br> 364.00 | 1.3-1.9: m, 7 H; 2.2: m, 1 H; 2.5: m, 1 H; 4.0: m, 1 H; 4.2: m, 1 H; 8.1: d, 2 H; 8.15: d, 2 H; 12.95: s, 1 H |
| 20 | 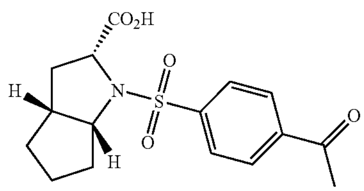 | Chiral | 337.39 <br> 338.05 | 1.3-1.8: m, 6 H; 1.9: m, 1 H; 2.15: m, 1 H; 2.45: m, 1 H; 2.65: s, 3 H; 3.9: m, 1 H; 4.15: m, 1 H; 7.95: d, 2 H; 8.15: d, 2 H; 12.8: s, 1 H |
| 21 | 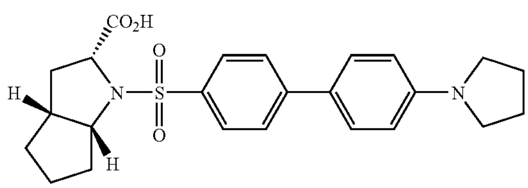 | Chiral | 440.56 <br> 441.09 | 1.3-1.8: m, 6 H; 1.9: m, 1 H; 2.0: m, 4 H; 2.15: m, 1 H; 2.45: m, 1 H; 3.3: m, 4 H; 3.9: m, 1 H; 4.05: m, 1 H; 6.6: d, 2 H; 7.6: d, 2 H; 7.8: m, 4 H |
| 22 | 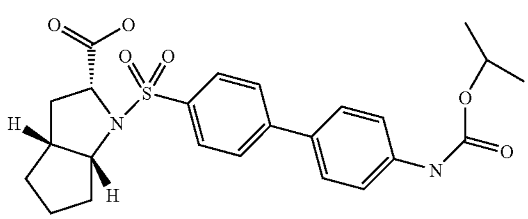 | Chiral | 472.56 <br> 473.16 | 11.3-1.8: m, 6 H; 1.35: d, 6 H; 1.9: m, 1 H; 2.2: m, 1 H; 2.45: m, 1 H; 3.9: s, 1 H; 4.0: s, 1 H; 4.9: s, 1 H; 7.6: d, 2 H; 7.8: d, 2 H; 7.8: m, 4 H; 10.0: s, 1 H |
| 23 | 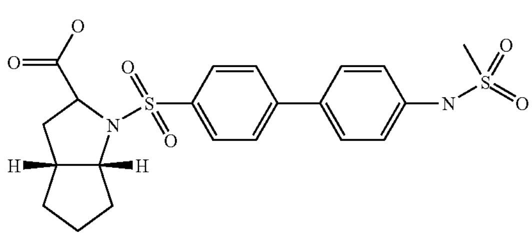 | | 464.56 <br> 465.20 | 1.3-1.9: m, 7 H; 2.1: m, 1 H; 2.4: m, 1 H; 3.0: s, 3 H; 3.9: s, 1 H; 4.05: s, 1 H; 7.35: d, 2 H; 7.8: d, 2 H; 7.9: m, 4 H; 9.9: s, 1 H |
| 24 | 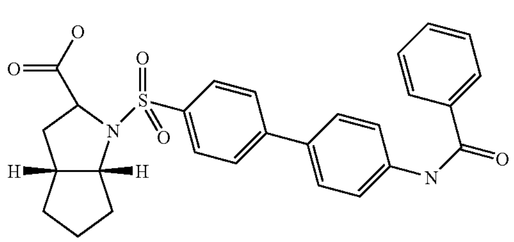 | | 490.58 <br> 491.34 | 1.3-1.9: m, 7 H; 2.1: m, 1 H; 2.4: m, 1 H; 3.95: m, 1 H; 4.1: m, 1 H; 7.55: m, 2 H; 7.8-8.1: m, 8 H; 8.4: m, 2 H |

-continued

| No. | Structure | | MS (ESI+) | NMR |
|---|---|---|---|---|
| 25 | 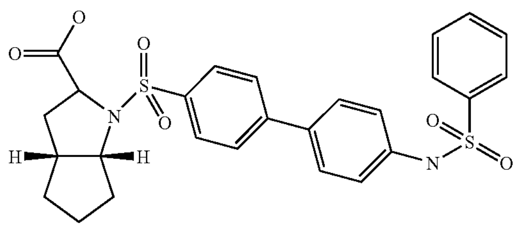 | | 526.63 527.12 | 1.3-1.8: m, 6 H; 1.8: m, 1 H; 2.0: m, 1 H; 2.1: m, 1 H; 3.85: m, 1 H; 4.05: m, 1 H; 7.2: m, 1 H; 7.6: m, 6 H; 7.9: m, 6 H |
| 26 | 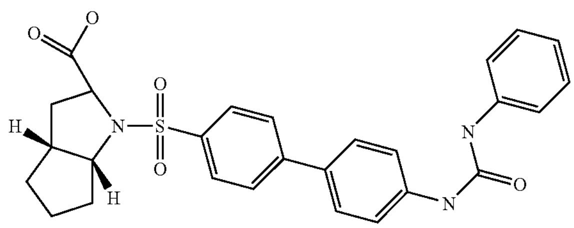 | | 505.59 506.28 | 1.3-1.8: m, 6 H; 1.9: m, 1 H; 2.15: m, 1 H; 2.45: m, 1 H; 3.9: m, 1 H; 4.1: m, 1 H; 7.0-8.5: m, 13 H; 12.8: s, 1 H |
| 27 | 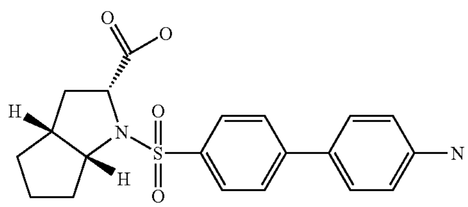 | Chiral | 386.47 387.14 | 1.3-1.8: m, 6 H; 1.85: m, 1 H; 2.1: m, 1 H; 2.4: m, 1 H; 3.85: m, 1 H; 4.1: m, 1 H; 8.1: d, 2 H; 8.3: d, 2 H |
| 28 | 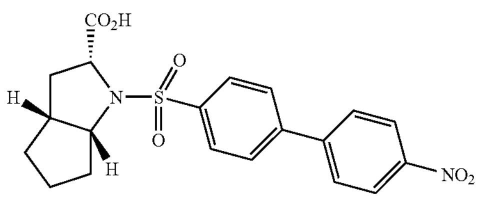 | Chiral | 416.46 417.23 | 1.3-1.8: m, 6 H; 1.9: m, 1 H; 2.15: m, 1 H; 2.45: m, 1 H; 3.95: m, 1 H; 4.10: m, 1 H; 8.0: m, 4 H; 8.1: d, 2 H; 8.3: d, 2 H |
| 29 | 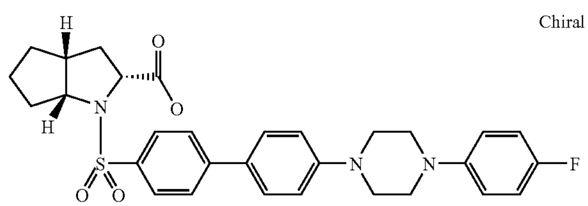 | Chiral | 549.67 550.37 | 1.3-1.8: m, 6 H; 1.9: m, 1 H; 2.15: m, 1 H; 2.45: m, 1 H; 3.25: m, 4 H; 3.4: m, 4 H; 3.9: m, 1 H; 4.05: m, 1 H; 7.1: m, 6 H; 7.7: d, 2 H; 7.9: m, 4 H; |
| 30 | 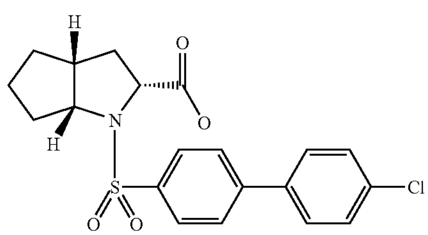 | Chiral | 405.90 406.21 | 1.3-1.8: m, 6 H; 1.9: m, 1 H; 2.2: m, 1 H; 2.45: m, 1 H; 3.9: m, 1 H; 4.1: m, 1 H; 7.6: d, 2 H; 7.8: d, 2 H; 7.95: m, 4 H |
| 31 | 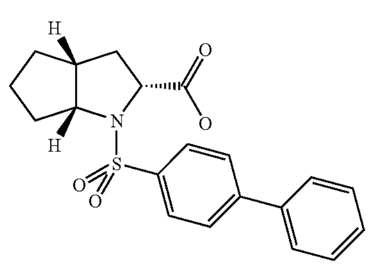 | | 371.46 372.16 | 1.3-1.8: m, 6 H; 1.9: m, 1 H; 2.2: m, 1 H; 2.45: m, 1 H; 3.9: m, 1 H; 4.1: m, 1 H; 7.5: m, 3 H; 7.75: m, 2 H; 7.95: m, 4 H |

-continued

| No. | Structure | | MS (ESI+) | NMR |
|---|---|---|---|---|
| 32 | 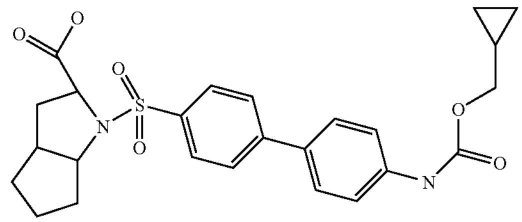 | | 484.58 485.12 | 0.35: m, 2 H; 0.55: m, 2 H; 1.3-1.8: m, 8 H; 1.95: m, 1 H; 2.3: m, 1 H; 3.95: 1 H; 4.2: m, 1 H; 7.6: m, 3 H; 7.85: m, 3 H; 8.05: m, 2 H |
| 33 | 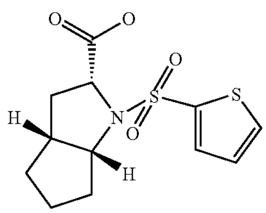 | Chiral | 301.39 302.06 | 1.3-1.8: m, 6 H; 1.9: m, 1 H; 2.2: m, 1 H; 2.4: m, 1 H; 3.9: m, 1 H; 4.05: m, 1 H; 7.3: m, 1 H; 7.7: m, 1 H; 8.0: m, 1 H |
| 34 | 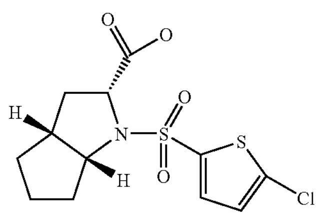 | Chiral | 335.83 336.01 | 1.3-1.8: m, 6 H; 1.9: m, 1 H; 2.15: m, 1 H; 2.5: m, 1 H; 3.95: m, 1 H; 4,: m, 1 H; 7.35: m, 1 H; 7.35: d, 1 H; 7.65: d, 1 H |
| 35 | 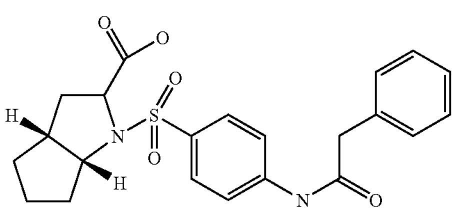 | | 428.51 429.24 | 1.3-1.7: m, 6 H; 1.9: m, 1 H; 2.1: m, 1 H; 2.4: m, 1 H; 3.8: m, 1 H; 4.0: m, 1 H; 7.3: m, 5 H; 7.8: d, 2 H; 7.85: d, 2 H; 10.8: s, 1 H |
| 36 | 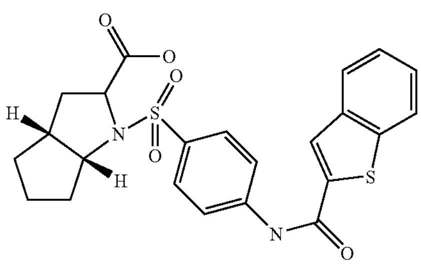 | | 470.57 471.22 | 1.3-1.7: m, 6 H; 1.85: m, 1 H; 2.1: m, 1 H; 2.45: m, 1 H; 3.9: m, 1 H; 4.1: m, 1 H; 7.5: m, 2 H; 7.9: d, 2 H; 8.05: m, 4 H; 8.45: s, 1 H; 10.9: s, 1 H |
| 37 | 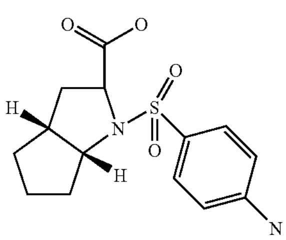 | | 310.09 311.13 | 1.3-1.7: m, 6 H; 1.85: m, 1 H; 2.1: m, 1 H; 2.4: m, 1 H; 3.8: m, 1 H; 3.9: m, 1 H; 6.6: d, 2 H; 7.45: d, 2 H; |

-continued

| No. | Structure | MS (ESI+) | NMR |
|---|---|---|---|
| 38 | Chiral | 386.88 387.14 | 1.3-2.0: m, 7 H; 2.2: m, 1 H; 2.55: m, 1 H; 4.2: m, 1 H; 4.25: m, 1 H; 7.65: d, 1 H; 8.2: s, 1 H; 8.7: d, 2 H |
| 39 | Chiral | 529.02 529.25 | 1.3-1.8: m, 6 H; 1.8: m, 1 H; 2.1: m, 1 H; 2.4: m, 1 H; 3.95: m, 1 H; 4.2: m, 1 H; 5.2: s, 2 H; 7.4: m, 5 H; 8.0: m, 2 H; 8.2: d, 1 H; 8.4: d, 1 H; 8.55: s, 1 H |
| 40 | Chiral | 558.69 559.32 | 1.2: s, 9H; 1.3-1.7: m, 6 H; 1.9: m, 1 H; 2.25: m, 1 H; 2.45: m, 1 H; 2.85: m, 2 H; 3.5: m, 2 H; 3.65: m, 1 H; 3.8: s, 3 H; 3.9: S. 3 H; 4.5: m, 1 H; 7.0: d, 1 H; 7.2: d, 1 H; 7.45: m, 2 H; 7.7: m, 2 H; 8.15: m, 1 H |
| 41 | Chiral | 474.56 475.21 | 1.3-1.8: m, 6 H; 2.0: m, 1 H; 2.3: m, 1 H; 2.6: m, 1 H; 2.9: m, 4 H; 3.6: m, 4 H; 3.8: m, 1 H; 4.1: s, 3 H; 4.5: m, 1 H; 7.5: d, 1 H; 7.95: d, 1 H; 8.05: d, 1 H |
| 42 | 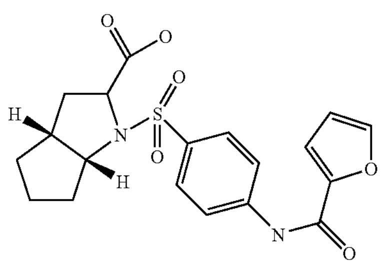 | 404.45 405.22 | 1.3-1.8: m, 6 H; 1.85: m, 1 H; 2.1: m, 1 H; 2.45: m, 1 H; 3.9: m, 1 H; 4.05: m, 1 H; 6.7: d, 1 H; 7.4: d, 1 H; 7.8: d, 2 H; 8.0: m, 3 H; 10.4: s, 1 H |
| 43 | 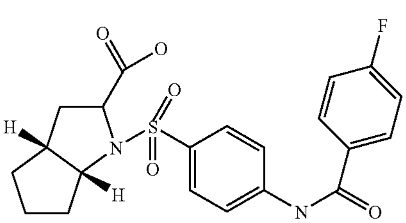 | 432.47 433.23 | 1.3-1.7: m, 6 H; 1.85: m, 1 H; 2.1: m, 1 H; 2.45: m, 1 H; 3.9: m, 1 H; 4.05: m, 1 H; 7.4: m, 2 H; 7.8: m, 2 H; 8.05: m, 4 H; 10.6: s, 1 H |

-continued
| No. | Structure | MS (ESI+) | NMR |
|---|---|---|---|
| 44 | 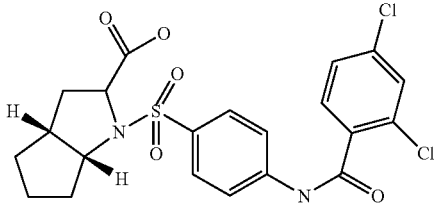 | 483.37 483.19 | 1.3-1.8: m, 6 H; 1.85: m, 1 H; 2.15: m, 1 H; 2.45: m, 1 H; 3.9: m, 1 H; 4.05: m, 1 H; 7.5: d, 1 H; 7.65: d, 1 H; 7.75: s, 1 H; 7.8: d, 2 H; 7.9: d, 2 H; 10.9: s, 1 H |
| 45 | 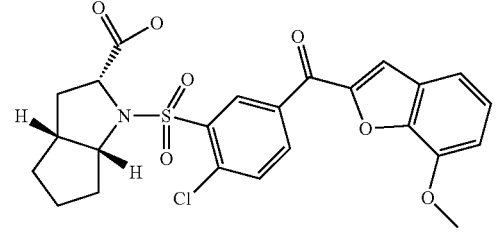 | 503.96 504.25 | 1.3-1.85: m, 6 H; 2.05: m, 1 H; 2.4: m, 1 H; 2.65: m, 1 H; 3.95: s, 3 H; 4.0: m, 1 H; 4.6: m, 1 H; 7.2: d, 2 H; 7.3: m, 1 H; 7.4: d, 1 H; 7.85: s, 1 H; 7.9: d, 1 H; 8.2: d, 1 H; 8.45: s, 1 H |
| 46 | 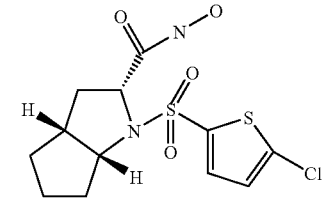 | Chiral 350.85 351.14 | 1.4-2.0: m, 8 H; 2.4: m, 1 H; 3.8: m, 1 H; 3.95: m, 1 H; 7.35: d, 1 H; 7.65: d, 1 H; 10.4: s, 1 H; |
| 47 | 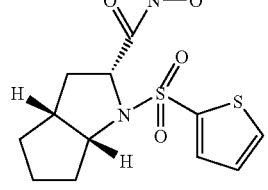 | Chiral 316.40 317.17 | 1.8-2.4: m, 8 H; 2.85: m, 1 H; 3.8: m, 1 H; 3.9: m, 1 H; 7.25: m, 1 H; 7.8: m, 1 H; 8.05: m, 1 H; 10.4: s, 1 H |
| 48 | 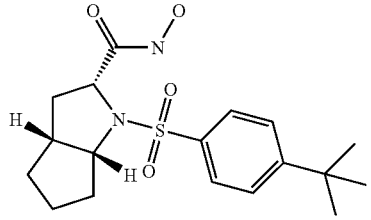 | Chiral 366.48 367.22 | 1.35: s, 9H; 1.4-1.95: m, 8 H; 2.35: m, 1 H; 3.8-4.0: m, 2 H; 7.6: d, 2 H; 7.8: d, 2 H; 10.55: s, 1 H |
| 49 | 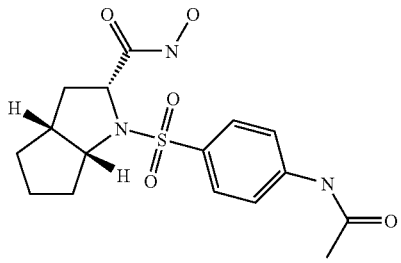 | Chiral 367.43 368.19 | 1.4-1.95: m, 8 H; 2.1: s, 3 H; 2.35: m, 1 H; 3.8-4.0: m, 2 H; 7.8: m, 4 H; 10.4: s, 1 H; 10.6: s, 1 H |

| No. | Structure | MS (ESI+) | NMR |
|---|---|---|---|
| 50 | 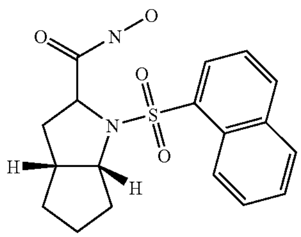 | Chiral 360.44 361.77 | 1.4-2.0: m, 8 H; 2.35: m, 1 H; 3.8-4.1: m, 2 H; 7.65: m, 2 H; 7.95: d, 1 H; 8.10: d, 1 H; 8.15: m, 2 H; 8.5: s, 1 H, 10.6: s, 1 H |
| 51 | 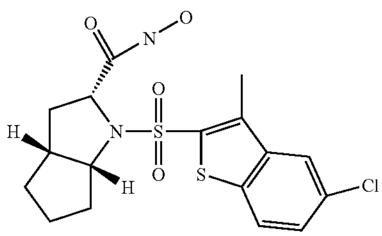 | Chiral 414.93 415.12 | 1.4-1.9: m, 7 H; 1.95-2.2: m, 2 H; 2.7: s, 3 H; 4.1: m, 2 H; 7.6: m, 1 H; 8.1: m, 2 H; 10.6: s, 1 H |
| 52 | 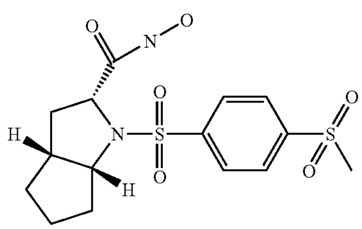 | Chiral 388.46 389.14 | 1.4-1.8: m, 8 H; 1.90: m, 1 H; 3.4: s, 3 H; 3.9: m, 2 H; 8.15: m, 4 H; 10.6: s, 1 H |
| 53 | 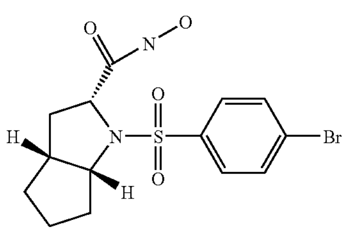 | Chiral 389.27 389.07 | 1.4-2.0: m, 8 H; 2.40: m, 1 H; 3.9: m, 2 H; 7.8: m, 4 H; 10.6: s, 1 H |
| 54 | 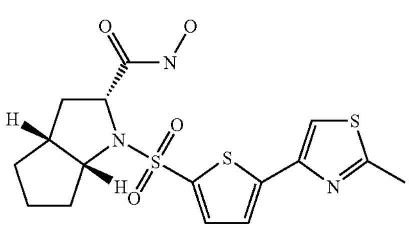 | Chiral 413.54 414.05 | N.A. |
| 55 | 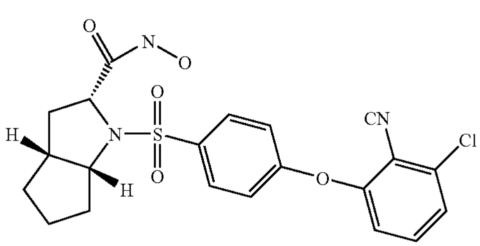 | Chiral 461.93 462.07 | 1.4-2.1: m, 8 H; 2.4: m, 1 H; 3.95: m, 2 H; 7.65: d, 1 H; 7.40: d, 1 H; 7.50: d, 1 H; 7.60: d, 1 H; 7.75: m, 1 H; 7.95: d, 2 H; 10.6: s, 1 H |

-continued

| No. | Structure | MS (ESI+) | NMR |
|---|---|---|---|
| 56 | 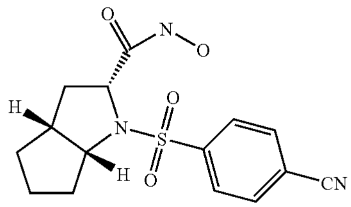 | Chiral 335.38 336.14 | 1.4-2.1: m, 8 H; 2.4: m, 1 H; 2.4: m, 1 H; 3.95: m, 2 H; 8.0: d, 2 H; 8.1: d, 2 H; 10.6: s, 1 H; |
| 57 | 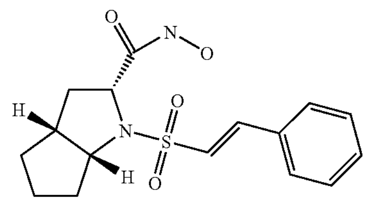 | Chiral 336.41 337.11 | 1.4-1.8: m, 6 H; 2.0: m, 1 H; 2.2: m, 1 H; 2.6: m, 1 H; 3.95: m, 1 H; 4.05: m, 1 H; 7.9: m, 4 H; 7.7: m, 2 H; 10.5: s, 1 H |
| 58 | 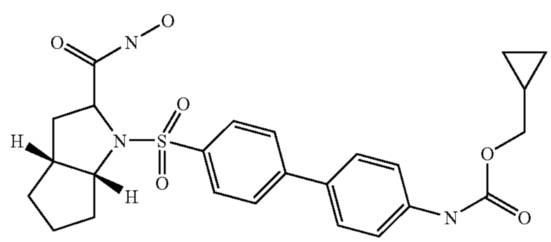 | 499.59 500.09 | 0.35: m, 2 H; 0.55: m, 2 H; 1.1-1.85: m, 9H; 1.95: m, 2 H; 2.35: m, 1 H; 3.85: m, 1 H; 3.95: m, 1 H; 7.60: d, 2 H; 7.7: d, 2 H; 7.9: m, 4 H; 9.8: s, 1 H; 10.6: s, 1 H |
| 59 | 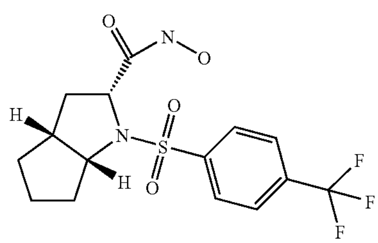 | Chiral 378.38 379.02 | 1.4-2.1: m, 8 H; 2.4: m, 1 H; 3.9: m, 2 H; 8.0: d, 2 H; 8.1: d, 2 H; 10.65: s, 1 H |
| 60 | 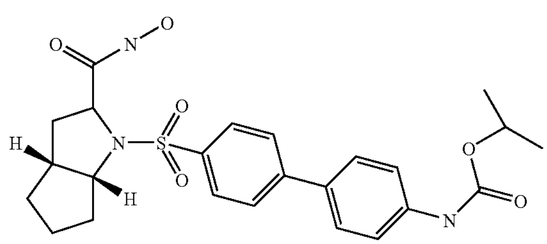 | 487.58 488.36 | 1.26: d, 6 H; 1.4-2.0: m, 8 H; 2.35: m, 1 H; 3.85: m, 2 H; 4.95: m, 1 H; 7.6: d, 2 H; 7.7: d, 2 H; 7.85: m, 4 H; 9.8: s, 1 H; 10.6: s, 1 H |
| 61 | 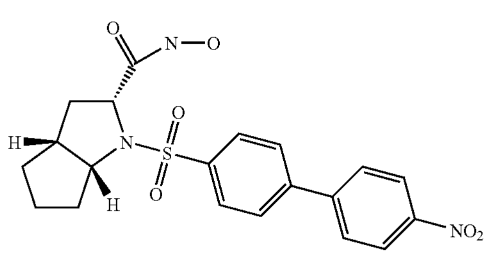 | Chiral 431.12 432.01 | 1.4-1.8: m, 8 H; 2.45: m, 1 H; 3.9: m, 2 H; 8.05: m, 6 H; 8.35: m, 2 H; 10.65: s, 1 H |

-continued

| No. | Structure | MS (ESI+) | NMR |
|---|---|---|---|
| 62 | Chiral | 420.92 421.24 | 1.4-1.8: m, 6 H; 2.0: m, 2 H; 2.4: m, 1 H; 3.95: m, 2 H; 7.6: d, 2 H; 7.8: d, 2 H; 8.0: m, 4 H; 10.6: s, 1 H |
| 63 | Chiral | 564.68 565.39 | 1.4-2.05: m, 8 H; 2.35: m, 1 H; 3.35: m, 4 H; 3.40: m, 4 H; 3.9: m, 2 H; 7.1: m, 6 H; 7.6: d, 2 H; 7.9: m, 4 H; 10.6: s, 1 H |
| 64 | Chiral | 386.47 387.19 | 1.4-2.0: m, 8 H; 2.45: m, 1 H; 3.95: m, 2 H; 7.45: m, 3 H; 7.75: m, 2 H; 7.95: m, 4 H; 10.6: s, 1 H |
| 65 | Chiral | 435.99 437.02 | 1.4-20: m, 8 H; 2.35: m, 1 H; 3.85: m, 2 H; 7.6: d, 2 H; 8.0: d, 2 H; 10.6: s, 1 H |
| 66 | Chiral | 355.08 356.09 | 1.4-2.0: m, 8 H; 2.35: m, 1 H; 3.95: m, 2 H; 8.15: d, 2 H; 8.4: d, 2 H; 10.6: s, 1 H |
| 67 | 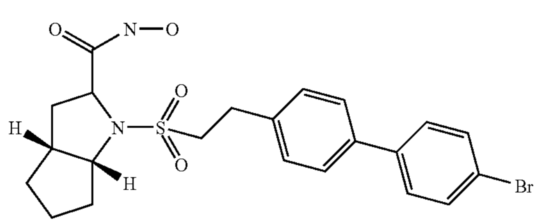 | 493.42 493.10 | 1.4-1.95: m, 8 H; 2.35: m, 1 H; 2.70: m, 2 H; 3.0: m, 2 H; 4.1: m, 1 H; 4.3: m, 1 H; 7.4: m, 2 H; 7.6: m, 6 H; 10.6: s, 1 H |

-continued

| No. | Structure | MS (ESI+) | NMR |
|---|---|---|---|
| 68 | 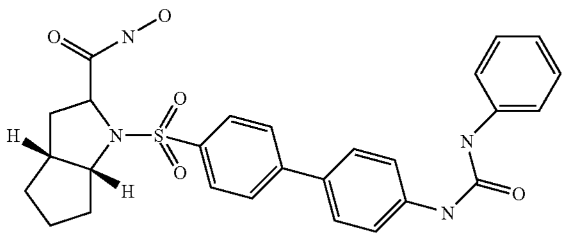 | 520.61<br>521.16 | 1.4-1.9: m, 8 H; 2.4: m, 1 H; 3.85: m, 2 H; 7.0-8.0: m, 12 H; 8.6: s, 1 H; 8.8: s, 1 H; 10.6: s, 1 H |
| 69 | 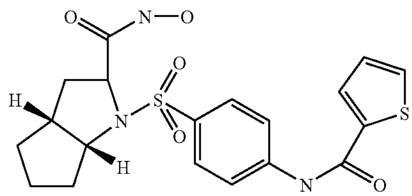 | 435.52<br>436.19 | 1.4-1.85: m, 6 H; 1.9: m, 2 H; 2.4: m, 1 H; 3.95: m, 2 H; 7.25: m, 1 H; 7.8-8.1: m, 6 H; 8.9: s, 1 H; 10.5: s, 1 H |
| 70 | 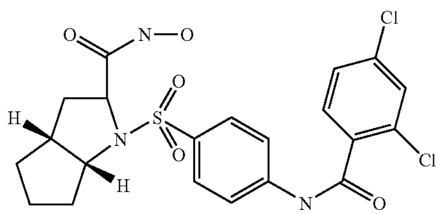 | 498.39<br>498.17 | 1.4-1.85: m, 6 H; 1.9: m, 2 H; 2.4: m, 1 H; 3.85: m, 2 H; 7.6-7.9: m, 7 H; 8.95: s, 1 H; 11.0: s, 1 H |
| 71 | 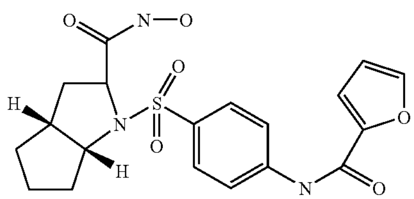 | 419.59<br>420.21 | 1.4-1.85: m, 6 H; 1.95: m, 2 H; 2.3: m, 1 H; 3.95: m, 2 H; 3.85: m, 2 H; 6.7: m, 1 H; 7.4: m, 1 H; 7.8: m, 2 H; 8.0: m, 3 H; 8.9: s, 1 H; 10.8: s, 1 H |
| 72 | 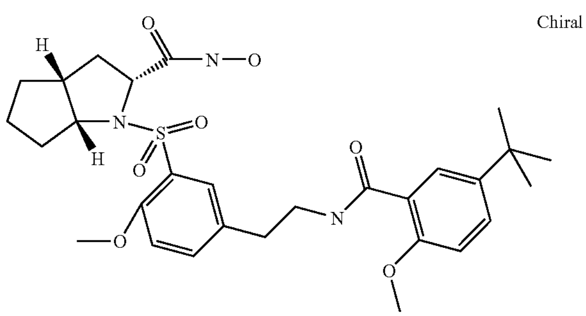 | Chiral 573.71<br>574.38 | 1.25: s, 9H; 1.3-1.8: m, 6 H; 1.9: m, 1 H; 2.1: m, 1 H; 2.4: m, 1 H; 2.85: m, 2 H; 3.5: m, 2 H; 3.8: s, 3 H; 3.9: s, 3 H; 4.3: m, 2 H; 7.0: d, 2 H; 7.2: d, 2 H; 7.5: m, 2 H; 7.7: d, 2 H; 8.1: m, 1 H; 10.2: s, 1 H |
| 73 | 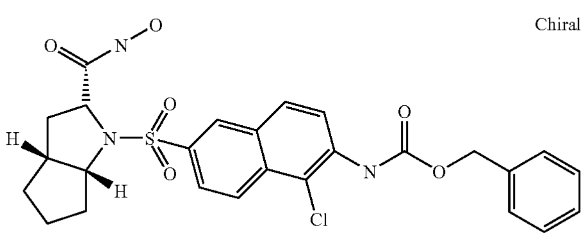 | Chiral 544.03<br>544.24 | 1.4-1.8: m, 6 H; 1.95: m, 2 H; 2.3: m, 1 H; 3.95: m, 2 H; 5.2: s, 2 H; 7.4: m, 6 H; 8.0: m, 2 H; 8.2: d, 1 H; 8.45: d, 1 H; 8.55: s, 1 H; 10.8: s, 1 H |

-continued

| No. | Structure | | MS (ESI+) | NMR |
|---|---|---|---|---|
| 74 | 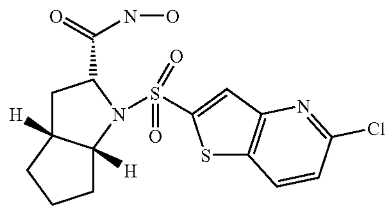 | Chiral | 401.89<br>402.13 | 1.4-1.9: m, 6 H; 2.05: m, 2 H;<br>2.4: m, 1 H; 3.95: m, 1 H; 4.1:<br>m, 1 H; 7.6: d, 1 H; 8.25: s, 1 H;<br>8.7: d, 1 H |
| 75 | 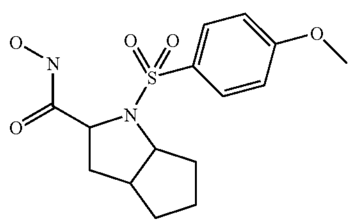 | | 340.11 | 1.4-2.0: m, 8 H; 2.3: m, 1 H;<br>3.8: m, 2 H; 3.85: s, 3 H; 7.17:<br>d, 2 H; 7.82: d, 2 H; 8.9: s, 1 H;<br>10.6: s, 1 H |
| 76 | 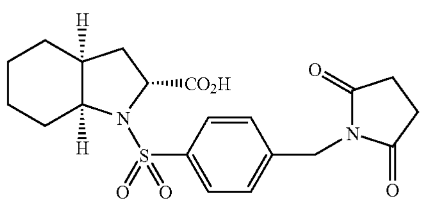 | | 420.49<br>421.02 | N.A. |
| 77 | 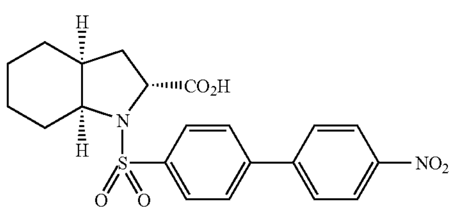 | Chiral | 430.48<br>431.17 | 1.0-1.9: m, 9 H; 1.85: m, 1 H;<br>2.45: m, 1 H; 3.75: m, 1 H;<br>4.3: m, 1 H; 8.0: m, 6 H; 8.4: m,<br>2 H |
| 78 | 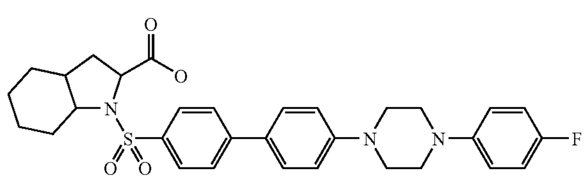 | | 563.70<br>564.35 | 1.0-1.95: m, 10 H; 2.4: m, 1 H;<br>3.25: m, 4 H; 3.45: m, 4 H; 3.75:<br>m, 1 H; 4.3: m, 1 H; 7.1: m, 6 H;<br>7.7: m, 2 H; 7.85: m, 4 H |
| 79 | 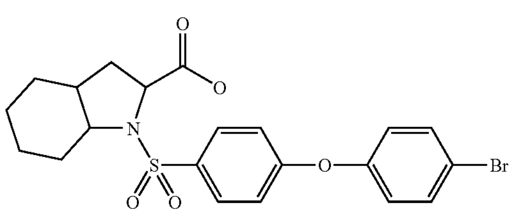 | | 480.38<br>482.16 | 1.0-1.9: m, 9 H; 2.35: m, 1 H;<br>2.4: m, 1 H; 3.7: m, 1 H; 4.2: m,<br>1 H; 7.1: m, 4 H; 7.6: m, 2 H;<br>7.8: m, 2 H |
| 80 | 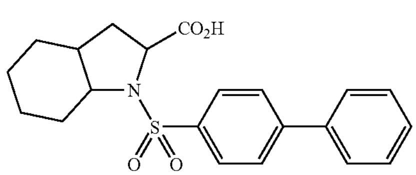 | | 371.46<br>372.16 | 1.3-1.9: m, 9 H; 2.2: m, 1 H;<br>2.45: m, 1 H; 3.9: m, 1 H; 4.1:<br>m, 1 H; 7.5: m, 3 H; 7.8: m, 3 H;<br>7.95: m, 4 H |

-continued

| No. | Structure | MS (ESI+) | NMR |
|---|---|---|---|
| 81 | 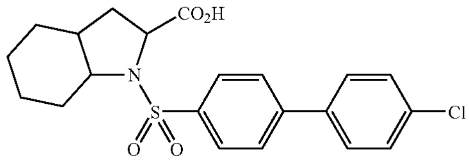 | 419.93<br>420.34 | 1.1-1.8: m, 9 H; 1.9: m, 1 H;<br>2.1: m, 1 H; 3.65: m, 1 H; 4.05:<br>pt, 1 H; 7.6: d, 2 H; 7.8: d,2 H;<br>7.9: m, 4 H |
| 82 | Chiral | 435.50<br>436.19 | 1.0-1.6: m, 8 H; 1.9: m, 1 H;<br>2.25: m, 1 H; 2.6: m, 1 H; 2.75:<br>m, 4 H; 3.6: m, 1 H; 4.1: m, 1 H;<br>7.4: d, 2 H; 7.8: d, 2 H |
| 83 | 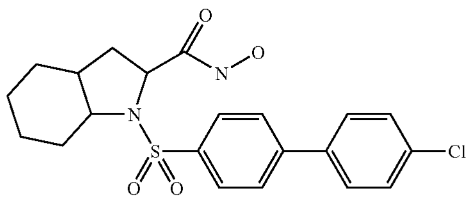 | 434.95<br>435.20 | 1.1-2.0: 11 H; 3.6: m, 1 H; 3.9:<br>m, 1 H; 7.6: d, 2 H; 7.8: d, 2 H;<br>7.95: d, 2 H; 8.0: d, 2 H |
| 84 | 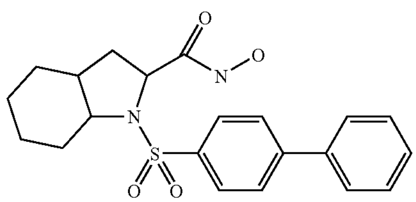 | 400.50<br>401.25 | 1.0-1.6: m, 8 H; 1.9: m, 1 H;<br>2.2: m, 1 H; 2.7: m, 1 H; 3.7: m,<br>1 H; 4.15: m, 1 H; 7.8: m, 4 H;<br>8.0: m, 2 H, 8.1: m, 2 H |

Pharmacological Examples

Preparing, and determining the enzymatic activity of the catalytic domain of human stromelysin (MMP-3) and neutrophilic collagenase (MMP-8).

The two enzymes, i.e., stromelysin (MMP-3) and neutrophilic collagenase (MMP-8), were prepared as described in Ye et al. (Biochemistry; 31 (1992) pages 11231-11235). For measuring enzymatic activity or the effect of an enzyme inhibitor, 70 µl of buffer solution and 10 µl of enzyme solution are incubated, for 15 minutes and at a physiological pH, with 10 µl of a 10% (v/v) aqueous solution of dimethyl sulfoxide containing the enzyme inhibitor, where appropriate. After 10 µl of a 10% (v/v) aqueous solution of dimethyl sulfoxide containing 1 mmol of the substrate/l have been added, the enzyme reaction is monitored by fluorescence spectroscopy (328 nm (ex)/393 nm(em)).

The enzyme activity is recorded as increase in extinction/minute. The $IC_{50}$ values listed in table 2 are determined as the inhibitor concentrations that in each case lead to 50% inhibition of the enzyme.

The buffer solution contains 0.05% Brij (Sigma, Deisenhofen, Germany) and also 0.1 mol of Tris/HCl/l, 0.1 mol of NaCl/l, 0.01 mol of $CaCl_2$/l and 0.1 mol of piperazine-N,N'-bis[2-ethanesulfonic acid]/l (pH=7.5). The enzyme solution contains 5 µg/ml of one of the enzyme domains prepared as described in Ye et al. The substrate solution contains 1 mmol of the fluorogenic substrate (7-methoxycoumarin-4-yl) acetyl-Pro-Leu-Gly-Leu-3-(2',4'-dinitrophenyl)-L-2,3-di-aminopropionyl-Ala-Arg-$NH_2$/A (Bachem, Heidelberg, Germany).

Determining the enzymatic activity of the catalytic domain of human collagenase 3 (MMP-13).

This protein is obtained from INVITEK, Berlin, as an inactive proenzyme (catalogue No. 30 100 803). Activating the proenzyme:

2 parts by volume of the proenzyme are incubated with 1 part by volume of APMA solution at 37° C. for 1.5 hours. The APMA solution is prepared from a 10 mmol/i solution of p-aminophenylmercuric acetate in 0.1 mmol/l NaOH by diluting with 3 parts by volume of Tris/HCl buffer, pH 7.5 (see below). The pH is adjusted to between 7.0 and 7.5 by adding 1 mmol of HCl/1. After the enzyme has been activated, it is diluted with the Tris/HCl buffer to a concentration of 1.67 µg/ml.

In order to measure the enzyme activity, 10 µl of enzyme solution are incubated for 15 minutes with 10 µl of a 3% (v/v) buffer solution of dimethyl sulfoxide (reaction 1). In order to measure enzyme inhibitor activity, 10 µl of enzyme solution are incubated with 10 µl of a 3% (v/v) buffer solution of dimethyl sulfoxide which contains the enzyme inhibitor (reaction 2).

Both in the case of reaction 1 and in the case of reaction 2, the enzyme reaction is monitored by fluorescence spectroscopy (328 nm (extinction)/393 nm (emission)) after 10 µl of a 3% (v/v) aqueous solution of dimethyl sulfoxide containing 0.75 mmol of the substrate/l have been added.

The enzyme activity is recorded as increase in extinction/minute.

The inhibitory effect is calculated as a percentage inhibition in accordance with the following formula:

% inhibition=100−[(increase in extinction/minute in reaction 2)/(increase in extinction/minute in reaction 1)×100].

The $IC_{50}$, i.e., the inhibitor concentration that is required for 50% inhibition of the enzyme activity, is determined graphically by plotting the percentage inhibitions at different inhibitor concentrations.

The buffer solution contains 0.05% Brij (Sigma, Deisenhofen, Germany) and also 0.1 mol of Tris/HCl/l, 0.1 mol of NaCl/l and 0.01 mol of $CaCl_2$/l (pH=7.5).

The enzyme solution contains 1.67 μg/ml of the enzyme domain.

The substrate solution contains 0.75 mmol of the fluorogenic substrate (7-methoxycoumarin-4-yl)acetyl-Pro-Leu-Gly-Leu-3-(2',4'-dinitrophenyl)-L-2,3-diaminopropionyl-Ala-Arg-$NH_2$/l (Bachem, Heidelberg, Germany).

The following table 2 shows the results.

TABLE 2

| Example No. | MMP-3 $IC_{50}$ (nM) | MMP-8 $IC_{50}$ (nM) | MMP-13 $IC_{50}$ (nM) |
|---|---|---|---|
| 13 | 200 | 200 | 700 |
| 21 | 160 | 4 | 100 |
| 29 | >10,000 | 10,000 | 260 |
| 57 | 330 | 320 | 200 |
| 61 | 22 | 3 | 2 |
| 63 | 200 | 3,700 | 4.2 |
| 64 | 100 | 20 | 3 |
| 65 | 300 | 100 | 220 |

The present invention may be embodied in other specific forms without departing from the spirit or essential attributes thereof.

What is claimed is:

1. A compound of formula I

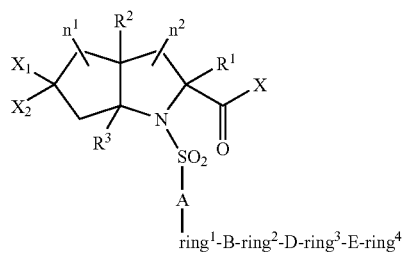

ring$^1$-B-ring$^2$-D-ring$^3$-E-ring$^4$ wherein
A is
—($C_0$-$C_4$)-alkylene,
B, D and E are identical or different and are, independently of each other,
—($C_0$-$C_4$)-alkylene,
—($C_2$-$C_4$)-alkenylene,
—S(O)$_o$—,
—NH—,
—NH—C(O)—,
—C(O)—NH—,
—NH—$SO_2$—,
—NH—C(O)—NH—,
—NH—C(S)—,
—NH—C(O)—O—,
—O—,
—O—C(O)—NH—,
—C(O)—,
—O—($CH_2$)$_n$—O—, or
—O—($CH_2$)$_m$—NH—,
o is
zero, 1 or 2,
n is
2 or 3,
m is
2 or 3,
ring$^1$, ring$^2$ or ring$^3$ are identical or different and are, independently of each other, covalent bond,
—($C_6$-$C_{14}$)-aryl that is unsubstituted or substituted, independently of each other, once, twice or three times, by G,
ring$^4$ is
—($C_6$-$C_{14}$)-aryl that is unsubstituted or substituted, independently of each other, once, twice or three times, by G,
G is
hydrogen,
halogen,
$R^4$,
—O—$R^4$,
—C(O)—$R^5$,
—S(O)$_p$—$R^4$,
—$NO_2$,
—CN or
—$NR^3R^4$,
p is
zero, 1 or 2,
X is
—NH—OH,
$X_1$ and $X_2$ are identical or different and are, independently of each other,
hydrogen or —($C_1$-$C_6$)-alkyl, or
taken together form the radical =O,
$n^1$ is
—($CH_2$)$_r$—,
$n^2$ is
—($CH_2$)$_q$—,
r is
1,
q is
1,
$R^1$ is
hydrogen, or
—($C_1$-$C_6$)-alkyl that is unsubstituted or substituted, once or twice, by —($C_3$-$C_6$)-cycloalkyl, —($C_6$-$C_{14}$)-aryl or heteroaryl,
$R^2$ and $R^3$ are identical or different and are, independently of each other,
hydrogen or —($C_1$-$C_6$)-alkyl,
R4 is
hydrogen,
—($C_1$-$C_6$)-alkyl that is unsubstituted or substituted, once, twice or three times, by halogen, —($C_3$-$C_6$)-cycloalkyl, —($C_6$-$C_{14}$)-aryl or heteroaryl,
—($C_6$-$C_{14}$)-aryl,
heteroaryl,
—C(O)—O—$R^5$,
—C(S)—O—$R^5$,
—C(O)—NH—$R^6$, or
—C(S)—NH—$R^6$, R5 is
- —(C$_1$-C$_6$)-alkyl that is unsubstituted or substituted, once or twice, by —(C$_3$-C$_6$)-cycloalkyl, —(C$_6$-C$_{14}$)-aryl or heteroaryl, and R6 is
- —(C$_1$-C$_6$)-alkyl that is unsubstituted or substituted, once or twice, by —(C$_3$-C$_6$)-cycloalkyl,
- —(C$_6$-C$_{14}$)-aryl or heteroaryl, or a stereoisomer therof, a mixture of stereoisomers thereof in any ratio, or physiologically tolerable salt thereof.

2. The compound of claim 1, wherein ring$^1$, ring$^2$ or ring$^3$ are
- —(C$_6$-C$_{14}$)-aryl that is phenyl, naphthyl, 1-naphthyl, 2-naphthyl, 4-biphenylyl, anthryl or fluorenyl and is unsubstituted or substituted, independently of each other, once, twice or three times, by G, ring$^4$ is
- —(C$_6$-C$_{14}$)-aryl that is phenyl, naphthyl, 1-naphthyl, 2-naphthyl, anthryl or fluorenyl and is unsubstituted or substituted, independently of each other, once, twice or three times, by G, R$^4$ is
- —(C$_1$-C$_6$)-alkyl that is unsubstituted or substituted, once, twice or three times, by halogen, —(C$_3$-C$_6$)-cycloalkyl, phenyl, naphthyl, acridinyl, azetidinyl, benzimidazolyl, benzofuranyl, benzothiofuranyl, benzothiophenyl, benzoxazolyl, benzothiazolyl, benzotriazolyl, benzotetrazolyl, benzisoxazolyl, benzisothiazolyl, benzimidazalinyl, carbazolyl, 4aH-carbazolyl, carbolinyl, chromanyl, chromenyl, cinnolinyl, deca-hydroquinolinyl, 2H,6H-1,5,2-dithiazinyl, dihydrofuran[2,3-b]tetrahydrofuran, furanyl, furazanyl, imidazolidinyl, imidazolinyl, imidazolyl, 1 H-indazolyl, indolinyl, indolizinyl, indolyl, 3H-indolyl, isobenzofuranyl, isochromanyl, isoindazolyl, isoindolinyl, isoindolyl, isoquinolinyl (benzimidazolyl), isothiazolyl, isoxazolyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, pyrimidinyl, phenanthridinyl, phenanthrolinyl, phenazinyl, phenothiazinyl, phenoxathiinyl, phenoxazinyl, phthalazinyl, piperazinyl, piperidinyl, pteridinyl, purinyl, pyranyl, pyrazinyl, pyroazolidinyl, pyrazolinyl, pyrazolyl, pyridazinyl, pyridooxazolyl, pyridoimidazolyl, pyridothiazolyl, pyridothiophenyl, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, 6H-1,2,5-thiadazinyl, 1,2,3-thiadiazolyl, 1, 2, 4-thiadiazolyl, 1, 2, 5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2,3-triazolyl, 1,2,3-triazolyl, 1,2,4-triazolyl, 1,2,5-triazolyl, 1,3,4-triazolyl or xanthenyl,
- —(C$_6$-C$_{14}$)-aryl that is phenyl or naphthyl, or heteroaryl that is acridinyl, azetidinyl, benzimidazolyl, benzofuranyl, benzothiofuranyl, benzothiophenyl, benzoxazolyl, benzothiazolyl, benzotriazolyl, benzotetrazolyl, benzisoxazolyl, benzisothiazolyl, benzimidazalinyl, carbazolyl, 4aH-carbazolyl, carbolinyl, chromanyl, chromenyl, cinnolinyl, deca-hydroquinolinyl, 2H,6H-1,5,2-dithiazinyl, dihydrofuran[2,3-b]tetrahydrofuran, furanyl, furazanyl, imidazolidinyl, imidazolinyl, imidazolyl, 1H-indazolyl, indolinyl, indolizinyl, indolyl, 3H-indolyl, isobenzofuranyl, isochromanyl, isoindazolyl, isoindolinyl, isoindolyl, isoquinolinyl (benzimidazolyl), isothiazolyl, isoxazolyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, pyrimidinyl, phenanthridinyl, phenanthrolinyl, phenazinyl, phenothiazinyl, phenoxathiinyl, phenoxazinyl, phthalazinyl, piperazinyl, piperidinyl, pteridinyl, purinyl, pyranyl, pyrazinyl, pyroazolidinyl, pyrazolinyl, pyrazolyl, pyridazinyl, pyridooxazolyl, pyridoimidazolyl, pyridothiazolyl, pyridothiophenyl, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, 6H-1,2,5-thiadazinyl, 1,2,3-thiadiazolyl, 1, 2, 4-thiadiazolyl, 1, 2, 5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2,3-triazolyl, 1,2,3-triazolyl, 1,2,4-triazolyl, 1,2,5-triazolyl, 1,3,4-triazolyl or xanthenyl, R$^5$ is
- —(C$_1$-C$_6$)-alkyl that is unsubstituted or substituted, once, twice or three times, by —(C$_3$-C$_6$)-cycloalkyl, phenyl, naphthyl, acridinyl, azetidinyl, benzimidazolyl, benzofuranyl, benzothiofuranyl, benzothiophenyl, benzoxazolyl, benzothiazolyl, benzotriazolyl, benzotetrazolyl, benzisoxazolyl, benzisothiazolyl, benzimidazalinyl, carbazolyl, 4aH-carbazolyl, carbolinyl, chromanyl, chromenyl, cinnolinyl, deca-hydroquinolinyl, 2H,6H-1,5,2-dithiazinyl, dihydrofuran[2,3-b]tetrahydrofuran, furanyl, furazanyl, imidazolidinyl, imidazolinyl, imidazolyl, 1H-indazolyl, indolinyl, indolizinyl, indolyl, 3H-indolyl, isobenzofuranyl, isochromanyl, isoindazolyl, isoindolinyl, isoindolyl, isoquinolinyl (benzimidazolyl), isothiazolyl, isoxazolyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, pyrimidinyl, phenanthridinyl, phenanthrolinyl, phenazinyl, phenothiazinyl, phenoxathiinyl, phenoxazinyl, phthalazinyl, piperazinyl, piperidinyl, pteridinyl, purinyl, pyranyl, pyrazinyl, pyroazolidinyl, pyrazolinyl, pyrazolyl, pyridazinyl, pyridooxazolyl, pyridoimidazolyl, pyridothiazolyl, pyridothiophenyl, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, 6H-1,2,5-thiadazinyl, 1,2,3-thiadiazolyl, 1, 2, 4-thiadiazolyl, 1, 2, 5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2,3-triazolyl, 1,2,3-triazolyl, 1,2,4-triazolyl, 1,2,5-triazolyl, 1,3,4-triazolyl or xanthenyl,
- —(C$_6$-C$_{14}$)-aryl that is phenyl or naphthyl, or heteroaryl that is acridinyl, azetidinyl, benzimidazolyl, benzofuranyl, benzothiofuranyl, benzothiophenyl, benzoxazolyl, benzothiazolyl, benzotriazolyl, benzotetrazolyl, benzisoxazolyl, benzisothiazolyl, benzimidazalinyl, carbazolyl, 4aH-carbazolyl, carbolinyl, chromanyl, chromenyl, cinnolinyl, deca-hydroquinolinyl, 2H,6H-1,5,2-dithiazinyl, dihydrofuran[2,3-b]tetrahydrofuran, furanyl, furazanyl, imidazolidinyl, imidazolinyl, imidazolyl, 1H-indazolyl, indolinyl, indolizinyl, indolyl, 3H-indolyl, isobenzofuranyl, isochromanyl, isoindazolyl, isoindolinyl, isoindolyl, isoquinolinyl (benzimidazolyl), isothiazolyl, isoxazolyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, pyrimidinyl, phenanthridinyl, phenanthrolinyl, phenazinyl, phenothiazinyl, phenoxathiinyl, phenoxazinyl, phthalazinyl, piperazinyl, piperidinyl, pteridinyl, purinyl, pyranyl, pyrazinyl, pyroazolidinyl, pyrazolinyl, pyrazolyl, pyridazinyl, pyridooxazolyl, pyridoimidazolyl, pyridothiazolyl, pyridothiophenyl, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, 6H-1,2,5-thiadazinyl, 1,2,3-thiadiazolyl, 1, 2, 4-thiadiazolyl, 1, 2, 5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2,3-triazolyl, 1,2,3-triazolyl, 1,2,4-triazolyl, 1,2,5-triazolyl, 1,3,4-triazolyl or xanthenyl, $R^6$ is
—($C_1$-$C_6$)-alkyl that is unsubstituted or substituted, once, twice or three times, by -($C_3$-$C_6$)-cycloalkyl, phenyl, naphthyl, acridinyl, azetidinyl, benzimidazolyl, benzofuranyl, benzothiofuranyl, benzothiophenyl, benzoxazolyl, benzothiazolyl, benzotriazolyl, benzotetrazolyl, benzisoxazolyl, benzisothiazolyl, benzimidazalinyl, carbazolyl, 4aH-carbazolyl, carbolinyl, chromanyl, chromenyl, cinnolinyl, deca-hydroquinolinyl, 2H,6H-1,5,2-dithiazinyl, dihydrofuran[2,3-b]tetrahydrofuran, furanyl, furazanyl, imidazolidinyl, imidazolinyl, imidazolyl, 1H-indazolyl, indolinyl, indolizinyl, indolyl, 3H-indolyl, isobenzofuranyl, isochromanyl, isoindazolyl, isoindolinyl, isoindolyl, isoquinolinyl (benzimidazolyl), isothiazolyl, isoxazolyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, pyrimidinyl, phenanthridinyl, phenanthrolinyl, phenazinyl, phenothiazinyl, phenoxathiinyl, phenoxazinyl, phthalazinyl, piperazinyl, piperidinyl, pteridinyl, purinyl, pyranyl, pyrazinyl, pyroazolidinyl, pyrazolinyl, pyrazolyl, pyridazinyl, pyridooxazolyl, pyridoimidazolyl, pyridothiazolyl, pyridothiophenyl, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, 6H-1,2,5-thiadazinyl, 1,2,3-thiadiazolyl, 1, 2, 4-thiadiazolyl, 1, 2, 5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2,3-triazolyl, 1,2,3-triazolyl, 1,2,4-triazolyl, 1,2,5-triazolyl, 1,3,4-triazolyl or xanthenyl, —($C_6$-$C_{14}$)-aryl that is phenyl or naphthyl, or heteroaryl that is acridinyl, azetidinyl, benzimidazolyl, benzofuranyl, benzothiofuranyl, benzothiophenyl, benzoxazolyl, benzothiazolyl, benzotriazolyl, benzotetrazolyl, benzisoxazolyl, benzisothiazolyl, benzimidazalinyl, carbazolyl, 4aH-carbazolyl, carbolinyl, chromanyl, chromenyl, cinnolinyl, deca-hydroquinolinyl, 2H,6H-1,5,2-dithiazinyl, dihydrofuran[2,3-b]tetrahydrofuran, furanyl, furazanyl, imidazolidinyl, imidazolinyl, imidazolyl, 1H-indazolyl, indolinyl, indolizinyl, indolyl, 3H-indolyl, isobenzofuranyl, isochromanyl, isoindazolyl, isoindolinyl, isoindolyl, isoquinolinyl (benzimidazolyl), isothiazolyl, isoxazolyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, pyrimidinyl, phenanthridinyl, phenanthrolinyl, phenazinyl, phenothiazinyl, phenoxathiinyl, phenoxazinyl, phthalazinyl, piperazinyl, piperidinyl, pteridinyl, purinyl, pyranyl, pyrazinyl, pyroazolidinyl, pyrazolinyl, pyrazolyl, pyridazinyl, pyridooxazolyl, pyridoimidazolyl, pyridothiazolyl, pyridothiophenyl, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, 6H-1,2,5-thiadazinyl, 1,2,3-thiadiazolyl, 1, 2, 4-thiadiazolyl, 1, 2, 5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2,3-triazolyl, 1,2,3-triazolyl, 1,2,4-triazolyl, 1,2,5-triazolyl, 1,3,4-triazolyl or xanthenyl, and $R^1$ is
—($C_1$-$C_6$)-alkyl that is unsubstituted or substituted, once, twice or three times, by —($C_3$-$C_6$)-cycloalkyl, phenyl, naphthyl, acridinyl, azetidinyl, benzimidazolyl, benzofuranyl, benzothiofuranyl, benzothiophenyl, benzoxazolyl, benzothiazolyl, benzotriazolyl, benzotetrazolyl, benzisoxazolyl, benzisothiazolyl, benzimidazalinyl, carbazolyl, 4aH-carbazolyl, carbolinyl, chromanyl, chromenyl, cinnolinyl, deca-hydroquinolinyl, 2H,6H-1,5,2-dithiazinyl, dihydrofuran[2,3-b]tetrahydrofuran, furanyl, furazanyl, imidazolidinyl, imidazolinyl, imidazolyl, 1H-indazolyl, indolinyl, indolizinyl, indolyl, 3H-indolyl, isobenzofuranyl, isochromanyl, isoindazolyl, isoindolinyl, isoindolyl, isoquinolinyl (benzimidazolyl), isothiazolyl, isoxazolyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, pyrimidinyl, phenanthridinyl, phenanthrolinyl, phenazinyl, phenothiazinyl, phenoxathiinyl, phenoxazinyl, phthalazinyl, piperazinyl, piperidinyl, pteridinyl, purinyl, pyranyl, pyrazinyl, pyroazolidinyl, pyrazolinyl, pyrazolyl, pyridazinyl, pyridooxazolyl, pyridoimidazolyl, pyridothiazolyl, pyridothiophenyl, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, 6H-1,2,5-thiadazinyl, 1,2,3-thiadiazolyl, 1, 2, 4-thiadiazolyl, 1, 2, 5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2,3-triazolyl, 1,2,3-triazolyl, 1,2,4-triazolyl, 1,2,5-triazolyl, 1,3,4-triazolyl or xanthenyl.

3. The compound of claim 1, wherein
B, D and E are identical or different and are, independently of each other,
—($C_0$-$C_2$)-alkylene,
—$C_2$-alkenylene,
—$S(O)_2$—,
—NH—,
—NH—C(O)—, —C(O)—NH—,
—NH—C(O)—NH—,
—O—, or
—C(O)—,
ring¹, ring² or ring³ are
—(C₆-C₁₄)-aryl that is phenyl or naphthyl and that is unsubstituted or substituted, independently of each other, once, twice or three times, by G,
ring⁴ is
—(C₆-C₁₄)-aryl that is phenyl or naphthyl and is unsubstituted or substituted, independently of each other, once, twice or three times, by G,
G is
halogen that is Br, Cl, I or F, or
—S(O)$_p$-R⁴ that is —S(O)₂-R⁴,
R⁴ is
hydrogen,
—(C₁-C₄)-alkyl that is unsubstituted or substituted, once, twice or three times, by Br, Cl, F, —C₃-cycloalkyl, phenyl, naphthyl, or heteroaryl that is benzofuranyl, benzothiophenyl, dihydrofuranyl, furanyl, morpholinyl, piperazinyl, piperidinyl, pyridinyl, pyridothiophenyl, pyrimidinyl, pyrrolyl, thiazolyl or thiophenyl and is unsubstituted or substituted, independently of each other, once, twice or three times, by G, phenyl or naphthyl, heteroaryl that is benzofuranyl, benzothiophenyl, dihydrofuranyl, furanyl, morpholinyl, piperazinyl, piperidinyl, pyridinyl, pyridothiophenyl, pyrimidinyl, pyrrolyl, thiazolyl or thiophenyl
—C(O)—O—R⁵, or
—C(O)—NH—R⁶,
R⁵ is
—(C₁-C₄)-alkyl that is unsubstituted or substituted, once or twice, by —C₃-cycloalkyl, phenyl, naphthyl or heteroaryl that is benzofuranyl, benzothiophenyl, dihydrofuranyl, furanyl, morpholinyl, piperazinyl, piperidinyl, pyridinyl, pyridothiophenyl, pyrimidinyl, pyrrolyl, thiazolyl or thiophenyl and is unsubstituted or substituted, independently of each other, once, twice or three times, by G, phenyl or naphthyl, or heteroaryl that is benzofuranyl, benzothiophenyl, dihydrofuranyl, furanyl, morpholinyl, piperazinyl, piperidinyl, pyridinyl, pyridothiophenyl, pyrimidinyl, pyrrolyl, thiazolyl or thiophenyl
R⁶ is
—(C₁-C₄)-alkyl, in which alkyl is unsubstituted or substituted, once or twice, by —C₃-cycloalkyl, phenyl, naphthyl or heteroaryl that is benzofuranyl, benzothiophenyl, dihydrofuranyl, furanyl, morpholinyl, piperazinyl, piperidinyl, pyridinyl, pyridothiophenyl, pyrimidinyl, pyrrolyl, thiazolyl or thiophenyl, or
heteroaryl that is benzofuranyl, benzothiophenyl, dihydrofuranyl, furanyl, morpholinyl, piperazinyl, piperidinyl, pyridinyl, pyridothiophenyl, pyrimidinyl, pyrrolyl, thiazolyl or thiophenyl,
$X_1$ and $X_2$ are
hydrogen,
$n^1$ and $n^2$ are
—(CH₂)—, or $n^1$ is —(CH₂)₂— and $n^2$ is —(CH₂)—,
R¹ is
hydrogen, and
R² and R³ are
hydrogen.

4. A process for preparing the compound of claim 1, comprising

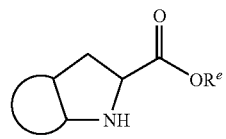

(IV)

wherein $R^e$ is hydrogen or an ester protecting group, with a compound of formula V,

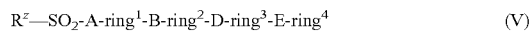

$R^z$—SO₂-A-ring¹-B-ring²-D-ring³-E-ring⁴      (V)

in which A, B, D, E and ring¹, ring², ring³ and ring⁴ are defined as in the compound of formula I, and wherein $R^z$ is a chlorine atom, imidazolyl or OH,
in the presence of a base, or after silylation with a suitable silylating agent, to give a compound of formula VI,

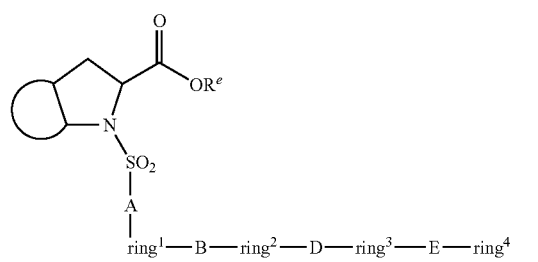

(VI)

wherein A, B, D, E, $R^e$ and ring¹, ring², ring³ and ring⁴ are as defined above, and
b) where $R^e$ is the ester protecting group, reacting a compound of formula VI, which has been prepared in accordance with step a), with a solution of an alkali such as NaOH or LiOH, and then treating with acid, to give the carboxylic acid of formula VII, with modifications in one of the side chains of ring¹-ring⁴ also having previously been carried out, where appropriate,

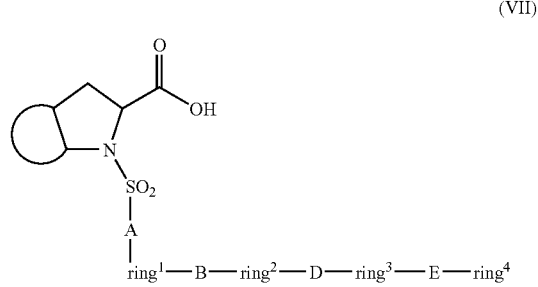

(VII)

and then converting this compound into the compound of formula I wherein X is NH—OH, and
c) optionally separating the compound of formula I, which has been prepared in accordance with steps a) or b) into an individual enantiomer by means of salt formation with an enantiomerically pure acid or base, chromatography on a chiral stationary phase or derivatization using chiral, enantiomerically pure compound, such as an amino acid, separation of the resulting derivatized diastereomers and elimination of the chiral auxiliary derivatization group, or d) optionally isolating the compound of formula I, which has been prepared in accordance with steps b) or c), in free form or, when an acidic or basic group is present, converting it into a corresponding physiologically tolerated salt.

5. A pharmaceutical preparation comprising a pharmaceutically effective amount of at least one compound according to claim 1 and a pharmaceutically tolerated carrier.

* * * * *

UNITED STATES PATENT AND TRADEMARK OFFICE
CERTIFICATE OF CORRECTION

| | | |
|---|---|---|
| PATENT NO. | : 7,772,270 B2 | Page 1 of 1 |
| APPLICATION NO. | : 11/405834 | |
| DATED | : August 10, 2010 | |
| INVENTOR(S) | : Schudok et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 303 days.

Signed and Sealed this
Twenty-second Day of March, 2011

David J. Kappos
*Director of the United States Patent and Trademark Office*